(12) United States Patent
Xiao et al.

(10) Patent No.: US 6,544,786 B1
(45) Date of Patent: Apr. 8, 2003

(54) METHOD AND VECTOR FOR PRODUCING AND TRANSFERRING TRANS-SPLICED PEPTIDES

(75) Inventors: Xiao Xiao, Waxford, PA (US); Paul Xiangoin Liu, Halifax (CA)

(73) Assignee: University of Pittsburgh of the Commonwealth of Higher Education, Pittsburgh, PA (US)

( * ) Notice: Subject to any disclaimer, the term of this patent is extended or adjusted under 35 U.S.C. 154(b) by 195 days.

(21) Appl. No.: 09/687,875

(22) Filed: Oct. 13, 2000

Related U.S. Application Data

(60) Provisional application No. 60/159,868, filed on Oct. 15, 1999.

(51) Int. Cl.[7] .......................... C12N 15/85; C12N 15/11; C12N 15/63; C07H 21/04; C07K 5/00
(52) U.S. Cl. ..................... 435/325; 435/69.1; 435/69.7; 435/91.4; 435/320.1; 435/337; 435/252.33; 530/333; 530/343; 536/23.1; 536/24.1
(58) Field of Search ............................. 435/69.1, 91.4, 435/320.1, 69.7, 337, 325; 424/184.1; 530/333, 343; 536/23.1, 24.1

(56) References Cited

U.S. PATENT DOCUMENTS

| | | | |
|---|---|---|---|
| 5,478,745 A | | 12/1995 | Samulski et al. |
| 5,496,714 A | * | 3/1996 | Comb et al. ............... 435/69.7 |
| 5,834,247 A | * | 11/1998 | Comb et al. ............... 435/69.7 |
| 5,858,351 A | | 1/1999 | Podsakoff et al. |
| 5,869,305 A | | 2/1999 | Samulski et al. |

FOREIGN PATENT DOCUMENTS

| | | |
|---|---|---|
| WO | WO-0071701 A1 * | 3/1996 |
| WO | WO 96/40272 | 12/1996 |

OTHER PUBLICATIONS

Belinda M. Lew et al., Protein Splicing in Vitro with a Semisynthetic Two–component Minimal Intein The Journal of Biological Chemistry, vol. 273, No. 26, pp. 15887–15890.*

Kane, P.M., Yamashiro, C.T., Wolczyk, D.F., Neff, N., Goebl, M., and Stevens, T.H. (1990), Protein splicing converts the yeast TFP1 gene product to the 69–kD subunit of the vacuolar H(+)–adenosine triphosphatase, *Science* 250, 651–657.

Perler, F.B., Davis, E.O., Dean, G.E., Gimble, F.S., Jack, W.E., Neff, N., Noren, C.J., Thorner, J., and Belfort, M. (1994), Protein splicing elements: inteins and exteins—a definition of terms and recommended nomenclature, *Nucleic Acids Res.* 22, 1125–1127.

Wallace, C.J. (1993), The curious case of protein splicing: mechanistic insights suggested by protein semisynthesis, *Protein Sci.* 2, 697–705.

Cooper, A.A., Chen, Y.J., Lindorfer, M.A., and Stevens, T.H. (1993), Protein splicing of the yeast TFP1 intervening protein sequence: a model for self–excision, *EMBO J.* 12, 2575–2583.

Xu, M.–Q., Southworth, M.W., Mersha, F.B., Hornstra, L.J., and Perler, F.B. (1993), In vitro protein splicing of purified precursor and the identification of a branched intermediate, *Cell* 75, 1371–1377.

Xu, M.–Q., Comb, D.G., Paulus, H., Noren, C.J., Shao, Y., and Perler, F.B. (1994), Protein splicing: an analysis of the branched intermediate and its resolution by succinimide formation, *EMBO J.* 13, 5517–5522.

Xu, M.–Q. and Perler, F.B, (1996), The mechanism of protein splicing and its modulation by mutation, *EMBO J.* 15, 5146–5153.

Southworth, M.W., Adam, E., Panne, D., Byer, R., Kautz, R., and Perler, F.B. (1998), Control of protein splicing by intein fragment reassembly, *EMBO J.* 17, 918–926.

Mills, K.V., Lew, B.M., Jiang, S.–Q., and Paulus, H. (1998), Protein splicing in trans by purified N– and C–terminal fragments of the *Mycobacterium tuberculosis* RecA intein, *Proc. Natl. Acad. Sci. U.S.A.* 95, 3543–3548.

Shingledecker, K., Jiang, S.–Q., and Paulus, H. (1998), Molecular dissection of the *Mycobacterium tuberculosis* RecA intein: design of a minimal intein of a trans–splicing system involved two intein fragments, *Gene* 207, 187–195.

Wu, H., Xu, M.–Q., and Liu, X.–Q (1998), Protein trans––splicing and functional mini–inteins of a cyanobacterial DnaB intein, *Biochim. Biophys. Acta* 1387, 422–432.

Wu, H., Hu, Z., and Liu, X.–Q. (1998), Protein trans–splicing by a split intein encoded in a split DnaE gene of synechocystis sp. PCC6803, *Proc. Natl. Acad. Sci. U.S.A.* 95, 9226–9231.

(List continued on next page.)

Primary Examiner—Sean McGarry
(74) Attorney, Agent, or Firm—Kirkpatrick & Lockhart LLP

(57) ABSTRACT

A method for trans-splicing peptides is provided. In the method, at least two extein peptides are provided, or are synthesized by recombinant methods, the extein peptides having co-reacting portions of a split intein attached thereto, so that the peptides will splice automatically under suitable conditions. A vector is also provided which includes at least one extein gene for expressing at least one of the extein peptides. Further provided is a method for circumventing packaging limitations in a gene delivery vehicle, by splitting a coding region for a protein to be delivered into two or more extein genes, which are packaged in separate virus particles and are co-delivered to a target cell for expression and for subsequent trans-splicing to form the complete protein. A pharmaceutical composition and a therapeutic method are also provided in which the recombinant viral particles are delivered to a cell and are expressed to produce a trans-spliced protein. In one embodiment, the protein to be trans-spliced is human dystrophin and the virus particle in which the extein genes are delivered is an Adeno-Associated Virus particle.

9 Claims, 13 Drawing Sheets

(1 of 13 Drawing Sheet(s) Filed in Color)

OTHER PUBLICATIONS

Emery, A.E.H., Duchenne Muscular Dystrophy, Oxford University Press, 1993: 392.

Straub, V. and Campbell, K.P. (1997), Muscular dystrophies and the dystrophin–glycoprotein complex, Curr. Opin. Neurol. 10, 168–175.

Brown, Jr., R.H. (1997), Dystrophin–associated proteins and the muscular dystrophies, Ann. Rev. Med. 48, 457–466.

Michalak, M. and Opas, M. (1997), Functions of dystrophin and dystrophin associated proteins, Curr. Opin. Neurol. 10, 436–442.

Monaco, A.P., Neve, R.L., Colletti–Feener, C., Bertelson, C.J., Kurnit, D.M., and Kunkel, L.M. (1986), Isolation of candidate cDNAs for portions of the Duchenne muscular dystrophy gene, Nature 323, 646–650.

Hoffman, E.P., Brown, Jr., R.H., and Kunkel, L.M. (1987), Dystrophin: the protein product of the Duchenne muscular dystrophy locus, Cell 51, 919–928.

Koenig, M., Hoffman, E.P., Bertelson, C.J., Monaco, A.P., Feener, C., and Kunkel, L.M. (1987), Complete cloning of the Duchenne muscular dystrophy (DMD) cDNA and preliminary genomic organization of the DMD gene in normal and affected individuals, Cell 50, 509–517.

Koenig, M., Monaco, A.P., and Kunkel, L.M. (1988), The complete sequence of dystrophin predicts a rod–shaped cytoskeletal protein, Cell 53, 219–226.

Karpati, G., Gilbert, R., Petrof. B.J., and Nalbantoglu, J. (1997), Gene therapy research for Duchenne and Becker muscular dystrophies, Curr. Opin. Neurol. 10, 430–435.

Gramolini, A.O., Angus, L.M., Schaeffer, L., Burton, E.A., Tinsley, J.M., Davies, K.E., Changeux, J.P., and Jasmin, B.J., (1999), Induction of utrophin gene expression by heregulin in skeletal muscle cells: role of the N–box motif and GA binding protein, Proc. Natl. Acad. Sci. U.S.A. 96, 3223, 3227.

Qu, Z., Balkir, L., van Duetekon, J.C., Robbins, P.D., Prochnic, R., and Huard, J. (1998), Development of approaches to improve cell survival in myoblast transfer therapy, J. Cell. Biol. 142, 1257–1267.

Moisset, P.A., Gagnon, Y., Karpati, G., and Tremblay, J.P. (1998a), Expression of human dystrophin following the transplation of genetically modified mdx myoblasts, Gene Ther. 5, 1340–1346.

Moisset, P.A., Skuk, D., Asselin, I., Goulet, M., Roy, B., Karpati, G., and Tremblay, J.P. (1998b), Successful transplantation of genetically corrected DMD myoblasts following ex vivo transduction with the dystrophin minigene, Biochem. Biophys. Res. Commun. 247, 94–99.

Miller, R.G., Sharma, K.R., Pavlath, G.K., Gussoni, E., Mynhier, M., Lanctot, A.M., Greco, C.M., Steinman, L., and Blau, H.M. (1997), Myoblast implantation in Duchenne muscular dystrophy: the San Francisco study, Muscle Nerve 20, 469–478.

Matsuo, M. (1996), Duchenne/Becker muscular dystrophy: from molecular diagnosis to gene therapy, Brain & Development 18, 167–172.

England, S.B., Nicholson, L.V.B., Johnson, M.A., Forrest, S.M., Love, D.R., Zubrzycka–Gaarn, E.E., Bulman, D.E., Harris, J.B., and Davies, K.E. (1990), Very mild muscular dystrophy associated with the deletion of 46% of dystrophin, Nature 343, 180–182.

Love, D.R., Flint, T.J., Sally, A.G., Middleton–Price, H.R., and Davies, K.E. (1991), Becker muscular dystrophy patient with a large intragenic dystrophin deletion: implications for functional minigenes and gene therapy, J. Med. Genet. 28, 860–864.

Li. J. Dressman, D., Tsao, Y.P., Sakamoto, A., Hoffman, E.P., and Xiao, X., rAAv Vector–mediated sarcoglycan gene transfer in a hamster model for limb girdle Muscular Dystrophy, Gene Therapy (1999) 6:74–82.

Greelish, J.P., Su, L.T., Lankford, E.B., Burkman, J.M., Chen, H., Konig, S.K., Mercier, I.M., Desjardins, P.R., Mitchell, M.A., Zheng, X.G., Leferovich, J., Gao, G.P., Balice–Gordon, R.J., Wilson, J.M., and Stedman, H.H. (1999), Stable restoration of the sarcoglycan complex in dystrophic muscle perfused with histamine and a recombinant adeno–associated viral vector, Nat. Med. 5, 439–43.

Perler, F.B., (1999), InBase, the New England Biolabs intein database, Nucleic Acids Res. 27:346–347 (with Intein database attachments from www.neb.com/neb/inteins).

Perler, F.B. (1998), Protein Splicing of inteins and Hedgehog autoproteolysis: structure, function, and evolution, Cell 92, 1–4.

Complete cDNA encoding human factor VIII; GenBank Accession No. E00527.

Homo Sapiens dystrophin (DMD) mRNA, complete cds; GenBank Accession No. M18533.

Homo sapiens ATP–binding cassette, sub–family A (ABC1), member 8 (ABCA8), mRNA; GenBank Accession No. NM_007168.

Homo sapiens dysferlin, limb girdle muscular dystrophy 2B (autosomal recessive) (DYSF), mRNA; GenBank Accession No. NM_003494.

Xiao, X., J. Li, and R. J. Samulski (1998), Production of high–titer recombinant adeno–associated virus vectors in the absence of helper adenovirus, Journal of Virology 72:2224–32.

Snyder, R., X. Xiao, and R. J. Samulski, 1996. Production of recombinant adeno–associated viral vectors, p. 12.1.1–12.2.23, In N. Dracopoli and J. Haines and B. Krof and D. Moir and C. Seidman and J. S. Seidman, D. (ed.), Current protocols in Human Genetics, John Wiley & Sons Ltd., New York.

Phelps, S. F., M. A. Hauser, N. M. Cole, J. A. Rafael, R. T. Hinkle, J. A. Faulkner, and J. S. Chamberlain. 1995, Expression of full–length and truncated dystrophin mini–genes in transgenic mdx mice, Hum Mol Genet. 4–1251–8.

* cited by examiner

```
ATGCTTTGGT GGGAAGAAGT AGAGGA CTGT TATGAAAGAG AAGATGTTCA GAAGAAAACA      60
TTCACAAAAT GGGTAAATGC ACAATTTTCT AAGTTTGGGA AGCAGCATAT TGAGAACCTC     120
TTCAGTGACC TACAGGATGG GAGGCGCCTC CTAGACCTCC TCGAAGGCCT GACAGGGCAA     180
AAACTGCCAA AGAAAAAGG ATCCACAAGA GTTCATGCCC TGAACAATGT CAACAGG GCA     240
CTGCGGGTTT TGCAGAACAA TAATGTTGAT TTAGTGAATA TTGGAAGTAC TGACATCGTA     300
GATGGAAATC ATAAACTGAC TCTTGGTTTG ATTTGGAATA TAATCCTCCA CTGGCAGGTC     360
AAAAATGTAA TGAAAAATAT CATGGCTGGA TTGCAACAAA CCAACAGTGA AAAGATTCTC     420
CTGAGCTGGG TCCGACAATC AACTCGTAAT TATCCACAGG TTAATGTAAT CAACTTCACC     480
ACCAGCTGGT CTGATGGCCT GGCTTTGAAT GCTCTCATCC ATAGTCATAG GCCAGACCTA     540
TTTGACTGGA ATAGTGTGGT TTGCCAGCAG TCAGCCACAC AACGACTGGA ACATGCATTC     600
AACATCGCCA GATATCAATT AGGCATAGAG AAACTACTCG ATCCTGAAGA T GTTGATACC     660
ACCTATCCAG ATAAGAAGTC CATCTTAATG TACATCACAT CACTCTTCCA AGTTTTGCCT     720
CAACAAGTGA GCATTGAAGC CATCCAGGAA GTGGAAATGT TGCCAAGGCC ACCTAAAGTG     780
ACTAAGAAG AACATTTTCA GTTACATCAT CAAATGCACT ATTCTCAACA GATCACGGTC     840
AGTCTAGCAC AGGGATATGA GAGAACTTCT TCCCCTAAGC CTCGATTCAA GAGCTATGCC     900
TACACACAGG CTGCTTATGT CACCACCTCT GACCCTACAC GGAGCCCATT TCCTTCACAG     960
CATTTGGAAG CTCCTGAAGA CAAGTCATTT GGCAGTTCAT TGATGGAGAG TGAAGTAAAC    1020
CTGGACCGTT ATCAAACAGC TTTAGAAGAA GTATTATCGT GGCTTCTTTC TGCTGAGGAC    1080
ACATTGCAAG CACAAGGAGA GATTTCTAAT GATGTGGAAG TGGTGAAAGA CCAGTTTCAT    1140
ACTCATGAGG GGTACATGAT GGATTTGACA GCCCATCAGG GCCGGGTTGG TAATATTCTA    1200
CAATTGGGAA GTAAGCTGAT TGGAACAGGA AAATTATCAG AAGATGAAGA AACTGAAGTA    1260
CAAGAGCAGA TGAATCTCCT AAATTCAAGA TGGGAATGCC TCAGGGTAGC TAGCATGGAA    1320
AAACAAAGCA ATTTACATAG AGTTTTAATG GATCTCCAGA ATCAGAAACT GAAAGAGTTG    1380
AATGACTGGC TAACAAAAAC AGAAGAAAGA ACAAGGAAAA TGGAGGAAGA GCCTCTTGGA    1440
```

FIG. 2/1

```
CCTGATCTTG AAGACCTAAA ACGCCAAGTA CAACAACATA AGGTGCTTCA AGAAGATCTA    1500

GAACAAGAAC AAGTCAGGGT CAATTCTCTC ACTCACATGG TGGTGGTAGT TGATGAATCT    1560

AGTGGAGATC ACGCAACTGC TGCTTTGGAA GAACAACTTA AGGTATTGGG AGATCGATGG    1620

GCAAACATCT GTAGATGGAC AGAAGACCGC TGGGTTCTTT TACAAGACAT CCTTCTCAAA    1680

TGGCAACGTC TTACTGAAGA ACAGTGCCTT TTTAGTGCAT GGCTTTCAGA AAAAGAAGAT    1740

GCAGTGAACA AGATTCACAC AACTGGCTTT AAAGATCAAA ATGAAATGTT ATCAAGTCTT    1800

CAAAAACTGG CCGTTTTAAA AGCGGATCTA GAAAAGAAAA AGCAATCCAT GGGCAAACTG    1860

TATTCACTCA ACAAGATCT TCTTT CAACA CTGAAGAATA AGTCAGTGAC CCAGAAGACG    1920

GAAGCATGGC TGGATAACTT TGCCCGGTGT TGGGATAATT TAGTCCAAAA ACTTGAAAAG    1980

AGTACAGCAC AGGAAACTGA AATAGCAGTT CAAGCTAAAC AACCGGATGT GGAAGAGATT    2040

TTGTCTAAAG GGCAGCATTT GTACAAGGAA AAACCAGCCA CTCAGCCAGT GAAGAG GAAG    2100

TTAGAAGATC TGAGCTCTGA GTGGAAGGCG GTAAACCGTT TACTTCAAGA GCTGAGGGCA    2160

AAGCAGCCTG ACCTAGCTCC TGGACTGACC ACTATTGGAG CCTCTCCTAC TCAGACTGTT    2220

ACTCTGGTGA CACAACCTGT GGTTACTAAG GAAACTGCCA TCTCCAAACT AGAAATGCCA    2280

TCTTCCTTGA TGTTGGAGGT ACCTGCTCTG GCAGATTTCA ACCGGGCTTG ACAGAACTT    2340

ACCGACTGGC TTTCTCTGCT TGATCAAGTT ATAAAATCAC AGAGGGTGAT GGTGGGTGAC    2400

CTTGAGGATA TCAACGAGAT GATCATCAAG CAGAAGGCAA CAATGCAGGA TTTGGAACAG    2460

AGGCGTCCCC AGTTGGAAGA ACTCATTACC GCTGCCCAAA ATTTGAAAAA CAAGACCAGC    2520

AATCAAGAGG CTAGAACAAT CATTACGGAT CGAATTGAAA GAATTCAGAA TCAGTGGGAT    2580

GAAGTACAAG AACACCTTCA GAACCGGAGG CAACAGTTGA ATGAAATGTT AAAGGATTCA    2640

ACACAATGGC TGGAAGCTAA GGAAGAAGCT GAGCAGGTCT TAGGACAGGC CAGAGCCAAG    2700

CTTGAGTCAT GGAA GGAGGG TCCCTATACA GTAGATGCAA TCCAAAAGAA AATCACAGAA    2760

ACCAAGCAGT TGGCCAAAGA CCTCCGCCAG TGGCAGACAA ATGTAGATGT GGCAAATGAC    2820

TTGGCCCTGA AACTTCTCCG GGATTA TTCT GCAGATGATA CCAGAAAAGT CCACATGATA    2880

ACAGAGAATA TCAATGCCTC TTGGAGAAGC ATTCATAAAA GGGTG AGTGA GCGAGAGGCT    2940
```

FIG. 2/2

```
GCTTTGGAAG AAACTCATAG ATTACTGCAA CAGTTCCCCC TGGACCTGGA AAAGTTTCTT    3000

GCCTGGCTTA CAGAAGCTGA ACAACTGCC  AATGTCCTAC AGGATGCTAC CCGTAAGGAA    3060

AGGCTCCTAG AAGACTCCAA GGGAGTAAAA GAGCTGATGA ACAATGGCA  AGACCTCCAA    3120

GGTGAAATTG AAGCTCACAC AGATGTTTAT CACAACCTGG ATGAAACAG  CCAAAAAATC    3180

CTGAGATCCC TGGAAGG TTC CGATGATGCA GTCCTGTTAC AAAGACGTTT GGATAACATG    3240

AACTTCAAGT GGAGTGAACT TCGGAAAAAG TCTCTCAACA TTAGGTCCCA TTTGGAAGCC    3300

AGTTCTGACC AGTGGAAGCG TCTGCACCTT T CTCTGCAGG AACTTCTGGT GTGGCTACAG    3360

CTGAAAGATG ATGAATTAAG CCGGCAGGCA CCTATTGGAG GCGACTTTCC AGCAGTTCAG    3420

AAGCAGAACG ATGTACATAG GGCCTTCAAG AGGGAATTGA AAACTAAAGA ACCTGTAATC    3480

ATGAGTACTC TTGAGACTGT ACGAATATTT CTGACAGAGC AGCCTTTGGA AGGACTAGAG    3540

AAACTCTACC AGGAGCCCAG AGAGCTGCCT CCTGAGGAGA GAGCCCAGAA TGTCACTCGG    3600

CTTCTACGAA AGCAGGCTGA GGAGGTCAAT ACTGAGTGGG AAAAATTGAA CCTGCACTCC    3660

GCTGACTGGC AGAGAAAAAT AGATGAGACC CTTGAAAGAC TCCAGGAACT TCAAGAGGCC    3720

ACGGATGAGC TGGACCTCAA GCTGCG CCAA GCTGAGGTGA TCAAGGGATC CTGGCAGCCC    3780

GTGGGCGATC TCCTCATTGA CTCTCTCCAA GATCACCTCG AGAAAGTCAA GGCACTTCGA    3840

GGAGAAATTG CGCCTCTGAA AGAGAACGTG AGCCACGTCA ATGACCTTGC TCGCCAGCTT    3900

ACCACTTTGG GCATTCAGCT CTCACCGTAT AACCTCAGCA CTCTGGAAGA CCTGAAC ACC    3960

AGATGGAAGC TTCTGCAGGT GGCCGTCGAG GACCGAGTCA GGCAGCTGCA TGAAGCCCAC    4020

AGGGACTTTG GTCCAGCATC TCAGCACTTT CTTTCCACGT CTGTCCAGGG TCCCTGGGAG    4080

AGAGCCATCT CGCCAAACAA AGTGCCCTAC TATATCAACC ACGAGACTCA AACAACTTGC    4140

TGGGACCATC CCAAAATGAC AGAGCTCTAC CAGTCTTTAG CTGACCTGAA TAATGTCAGA    4200

TTCTCAGCTT ATAGGACTGC CATGAAACTC CGAAGACTGC AGAAGGCCCT TTGCTTGGAT    4260

CTCTTGAGCC TGTCAGCTGC ATGTGATGCC TTGGACCAGC ACAACCTCAA GCAAAATGAC    4320

CAGCCCATGG ATATCCTGCA GATTATTAAT TGTTTGACCA CTATTTATGA C CGCCTGGAG    4380

CAAGAGCACA ACAATTTGGT CAACGTCCCT CTCTGCGTGG ATATGTGTCT GAACTGGCTG    4440

CTGAATGTTT ATGATACGGG ACGAACAGGG AGGATCCGTG TCCTGTCTTT TAAAACTGGC    4500
```

```
ATCATTTCCC TGTGTAAAGC ACATTTGGAA GACAAGTACA GATACCTTTT CAAGCAAGTG   4560

GCAAGTTCAA CAGGATTTTG TGACCAGCGC AGGCTGGGCC TCCTTCTGCA TGATTCTATC   4620

CAAATTCCAA GACAGTTGGG TGAAGTTGCA TCCTTTGGGG GCAGTAACAT TGAGCCAAGT   4680

GTCCGGAGCT GCTTCCAATT TGCTAATAAT AAGCCAGAGA TCGAAGCGGC CCTCTTCCTA   4740

GACTGGATGA GACTGGAACC CCAGTCCATG GTGTGGCT GC CCGTCCTGCA CAGAGTGGCT   4800

GCTGCAGAAA CTGCCAAGCA TCAGGCCAAA TGTAACATCT GCAAAGAGTG TCCAATCATT   4860

GGATTCAGGT ACAGGAGTCT AAAGCACTTT AATTATGACA TCTGCCAAAG CTGCTTTTTT   4920

TCTGGTCGAG TTGCAAAAGG CCATAAAATG CACTATCCCA TGGTGGAATA TTGCACTCCG   4980

ACTACATCAG GAGAAGATGT TCGAGACTTT GCCAAGGTAC TAAAAAACAA ATTTCGAACC   5040

AAAAGGTATT TTGCGAAGCA TCCCCGAATG GGCTACCTGC CAGTGCAGAC TGTCTTAGAG   5100

GGGGACAACA TGGAAACTCC CGTTACTCTG ATCAACTTCT GGCCAGTAGA TTCTGCGCCT   5160

GCCTCGTCCC CTCAGCTTTC ACACGATGAT ACTCATTCAC GCATTGAACA TTATGCTAGC   5220

AGGCTAGCAG AAATGGAAAA CAGCAATGGA TCTTATCTAA ATGATAGCAT CTCTCCTAAT   5280

GAGAGCATAG ATGATGAACA TTTGTTAATC CAGCATTACT GCCAAAGTTT GAACCAGGAC   5340

TCCCCCCTGA GCCAGCCTCG TAGTCCTGCC CAGATCTTGA TTTCCTTAGA GAGTGAGGAA   5400

AGAGGGGAGC TAGAGAGAAT CCTAGCAGAT CTTGAGGAAG AAAACAGGAA TCTGCAAGCA   5460

GAATATGACC GTCTAAAGCA GCAGCACGAA CATAAAGGCC TGTCCCCACT GCCGTCCCCA   5520

CCTGAAATGA TGCCCACCTC TCCCCAGAGT CCCCGGGATG CTGAGCTCAT TGCTGAGGCC   5580

AAGCTACTGC GTCAGCACAA AGGCCGC CTG GAAGCCAGGA TGCAAATCCT GGAAGACCAC   5640

AATAAACAGC TGGAGTCACA GTTACACAGG CTAAGGCAGC TGCTGGAGCA ACCCCAGGCA   5700

GAGGCCAAAG TGAATGGCAC AACGGTGTCC TCTCCTTCTA CCTCTCTACA GAGGTCCGAC   5760

AGCAGTCAGC CTATGCTGCT CCGAGTGGTT GGCAGTCAAA CTTCGGACTC CATGGGTG AG   5820

GAAGATCTTC TCAGTCCTCC CCAGGACACA AGCACAGGGT TAGAGGAGGT GATGGAGCAA   5880

CTCAACAACT CCTTCCCTAG TTCAAGAGGA AGAAATACCC CTGGAAAGCC AATGAGAGAG   5940

GACACAATGT AG                                                      5952
```

FIG. 2/4

```
TGCATCAGTG GAGATAGTTT GATCAGCTTG GCGAGCACAG GAAAAAGAGT TTCTATTAAA      60

GATTTGTTAG ATGAAAAAGA TTTTGAAATA TGGGCAATTA ATGAACAGAC GATGAAGCTA     120

GAATCAGCTA AAGTTAGTCG TGTATTTTGT ACTGGCAAAA AGCTAGTTTA TATTTTAAAA     180

ACTCGACTAG GTAGAACTAT CAAGGCAACA GCAAATCATA GA TTTTTAAC TATTGATGGT    240

TGGAAAAGAT TAGATGAGCT ATCTTTAAAA GAGCATATTG CTCTACCCCG TAAACTAGAA     300

AGCTCCTCTT TACAATTATA ATGAGGAGGT TTAAAATATG TCACCAGAAA TAGAAAAGTT     360

GTCTCAGAGT GATATTTACT GGGACTCCAT CGTTTCTATT ACGGAGACTG GAGTCGAAGA     420

GGTTTTTGAT TTGACTGTGC CAGGACCACA TAACTTTGTC GCCAATGACA TCATTGTCCA     480

TAAT                                                                 484
```

FIG. 4

```
ttggccctga aacttcttcg cgattatTGC CTCAGTTTTG GCACCGAAAT TTTAACCGTT    60

GAGTACGGCC CATTGCCCAT TGGCAAAATT GTGAGTGAAG AAATTAATTG TTCTGTGTAC   120

AGTGTTGATC CAGAAGGGAG AGTTTACACC CAGGCGATCG CCCAATGGCA TGACCGGGGA   180

GAGCAGGAAG TATTGGAATA TGAATTGGAA GATGGTTCAG  TAATCCGAGC TACCTCTGAC   240

CACCGCTTTT TAACCACCGA TTATCAACTG TTGGCGATCG AAGAAATTTT TGCTAGGCAA   300

CTGGACTTGT TGACTTTAGA AAATATTAAG CAAACTGAAG AAGCTCTTGA CAACCATCGT   360

CTTCCCTTTC CATTACTTGA CGCCGGAGGT TAAtcaacat atgacatgga tagtttctaa   420
tttaattaat cagcatcaaa aaatccctca aggcttcaca ataatccctg ttgttATGGT   480

TAAAGTTATC GGTCGTCGTT CCCTCGGAGT GCAAAGAATA TTTGATATTG GTCTTCCCCA   540

AGACCATAAT TTTCTGCTAG CCAATGGGGC GATCGCCGCC AATTCCGCGG ATGATACCAG   600

AAAAGTCCAC AT                                                       612
```

FIG. 6

SEQUENCE LISTING

<160> NUMBER OF SEQ ID NOS: 22

<210> SEQ ID NO 1
<211> LENGTH: 5952
<212> TYPE: DNA
<213> ORGANISM: Homo sapiens
<220> FEATURE:
<221> NAME/KEY: misc_feature
<222> LOCATION: (2897)..(2898)
<223> OTHER INFORMATION: S4 junction site
<221> NAME/KEY: misc_feature
<222> LOCATION: (3198)..(3199)
<223> OTHER INFORMATION: S2 junction site

<400> SEQUENCE: 1

| | | | | | | |
|---|---|---|---|---|---|---|
| atgctttggt | gggaagaagt | agaggactgt | tatgaaagag | aagatgttca | gaagaaaaca | 60 |
| ttcacaaaat | gggtaaatgc | acaattttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacagggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaaatat | catggctgga | ttgcaacaaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttctttc | tgctgaggac | 1080 |

```
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga acagtgcctt tttagtgcat ggctttcaga aaagaagat    1740 gcagtgaaca agattcacac aactggcttt aaagatcaaa atgaaatgtt atcaagtctt    1800
caaaaactgg ccgttttaaa agcggatcta gaaagaaaa agcaatccat gggcaaactg    1860
tattcactca aacaagatct tctttcaaca ctgaagaata agtcagtgac ccagaagacg    1920
gaagcatggc tggataactt tgcccggtgt tgggataatt tagtccaaaa acttgaaaag    1980
agtacagcac aggaaactga aatagcagtt caagctaaac aaccggatgt ggaagagatt    2040
ttgtctaaag gcagcatttt gtacaaggaa aaaccagcca ctcagccagt gaagaggaag    2100
ttagaagatc tgagctctga gtggaaggcg gtaaaccgtt tacttcaaga gctgagggca    2160
aagcagcctg acctagctcc tggactgacc actattggag cctctcctac tcagactgtt    2220
actctggtga cacaacctgt ggttactaag gaaactgcca tctccaaact agaaatgcca    2280
tcttccttga tgttggaggt acctgctctg gcagatttca accgggcttg gacagaactt    2340
accgactggc tttctctgct tgatcaagtt ataaaatcac agagggtgat ggtgggtgac    2400
cttgaggata tcaacgagat gatcatcaag cagaaggcaa caatgcagga tttgaacag    2460 aggcgtcccc agttggaaga actcattacc gctgcccaaa atttgaaaaa caagaccagc    2520
aatcaagagg ctagaacaat cattacggat cgaattgaaa gaattcagaa tcagtgggat    2580
gaagtacaag aacaccttca gaaccggagg caacagttga atgaaatgtt aaaggattca    2640
acacaatggc tggaagctaa ggaagaagct gagcaggtct taggacaggc cagagccaag    2700
cttgagtcat ggaaggaggg tccctataca gtagatgcaa tccaaaagaa aatcacagaa    2760
accaagcagt tggccaaaga cctccgccag tggcagacaa atgtagatgt ggcaaatgac    2820
ttggccctga aacttctccg ggattattct gcagatgata ccagaaaagt ccacatgata    2880
acagagaata tcaatgcctc ttggagaagc attcataaaa gggtgagtga gcgagaggct    2940
gctttggaag aaactcatag attactgcaa cagttcccc tggacctgga aaagtttctt    3000
gcctggctta cagaagctga aacaactgcc aatgtcctac aggatgctac ccgtaaggaa    3060
aggctcctag aagactccaa gggagtaaaa gagctgatga acaatggca agacctccaa    3120 ggtgaaattg aagctcacac agatgtttat cacaacctgg atgaaaacag ccaaaaaatc    3180
ctgagatccc tggaaggttc cgatgatgca gtcctgttac aaagacgttt ggataacatg    3240
aacttcaagt ggagtgaact tcggaaaaag tctctcaaca ttaggtccca tttggaagcc    3300
agttctgacc agtggaagcg tctgcacctt tctctgcagg aacttctggt gtggctacag    3360
ctgaaagatg atgaattaag ccggcaggca cctattggag gcgactttcc agcagttcag    3420
```

```
aagcagaacg atgtacatag ggccttcaag agggaattga aaactaaaga acctgtaatc    3480
atgagtactc ttgagactgt acgaatattt ctgacagagc agcctttgga aggactagag    3540
aaactctacc aggagcccag agagctgcct cctgaggaga gagcccagaa tgtcactcgg    3600
cttctacgaa agcaggctga ggaggtcaat actgagtggg aaaaattgaa cctgcactcc    3660
gctgactggc agagaaaaat agatgagacc cttgaaagac tccaggaact tcaagaggcc    3720
acggatgagc tggacctcaa gctgcgccaa gctgaggtga tcaagggatc ctggcagccc    3780
gtgggcgatc tcctcattga ctctctccaa gatcacctcg agaaagtcaa ggcacttcga    3840
ggagaaattg cgcctctgaa agagaacgtg agccacgtca atgaccttgc tcgccagctt    3900
accactttgg gcattcagct ctcaccgtat aacctcagca ctctggaaga cctgaacacc    3960
agatggaagc ttctgcaggt ggccgtcgag gaccgagtca ggcagctgca tgaagcccac    4020
agggactttg gtccagcatc tcagcacttt ctttccacgt ctgtccaggg tccctgggag    4080
agagccatct cgccaaacaa agtgccctac tatatcaacc acgagactca aacaacttgc    4140
tgggaccatc ccaaaatgac agagctctac cagtctttag ctgacctgaa taatgtcaga    4200
ttctcagctt ataggactgc catgaaactc cgaagactgc agaaggccct ttgcttggat    4260
ctcttgagcc tgtcagctgc atgtgatgcc ttggaccagc acaacctcaa gcaaaatgac    4320
cagcccatgg atatcctgca gattattaat tgtttgacca ctatttatga ccgcctggag    4380
caagagcaca caaatttggt caacgtccct ctctgcgtgg atatgtgtct gaactggctg    4440
ctgaatgttt atgatacggg acgaacaggg aggatccgtg tcctgtcttt taaaactggc    4500
atcatttccc tgtgtaaagc acatttggaa gacaagtaca gataccttt caagcaagtg    4560
gcaagttcaa caggatttg tgaccagcgc aggctgggcc tccttctgca tgattctatc    4620
caaattccaa gacagttggg tgaagttgca tcctttgggg gcagtaacat tgagccaagt    4680
gtccggagct gcttccaatt tgctaataat aagccagaga tcgaagcggc cctcttccta    4740
gactggatga gactggaacc ccagtccatg tgtggctgc ccgtcctgca cagagtggct    4800
gctgcagaaa ctgccaagca tcaggccaaa tgtaacatct gcaaagagtg tccaatcatt    4860
ggattcaggt acaggagtct aaagcacttt aattatgaca tctgccaaag ctgcttttt    4920
tctggtcgag ttgcaaaagg ccataaaatg cactatccca tggtgaata ttgcactccg    4980
actacatcag gagaagatgt tcgagacttt gccaaggtac taaaaaacaa atttcgaacc    5040
aaaaggtatt ttgcgaagca tccccgaatg ggctacctgc cagtgcagac tgtcttagag    5100
ggggacaaca tggaaactcc cgttactctg atcaacttct ggccagtaga ttctgcgcct    5160
gcctcgtccc ctcagctttc acacgatgat actcattcac gcattgaaca ttatgctagc    5220
aggctagcag aaatggaaaa cagcaatgga tcttatctaa atgatagcat ctctcctaat    5280
gagagcatag atgatgaaca tttgttaatc cagcattact gccaaagttt gaaccaggac    5340
tccccctga gccagcctcg tagtcctgcc cagatcttga tttccttaga gagtgaggaa    5400
agagggagc tagagagaat cctagcagat cttgaggaag aaaacaggaa tctgcaagca    5460
gaatatgacc gtctaaagca gcagcacgaa cataaaggcc tgtccccact gccgtcccca    5520
cctgaaatga tgcccacctc tccccagagt ccccgggatg ctgagctcat tgctgaggcc    5580
aagctactgc gtcagcacaa aggccgcctg gaagccagga tgcaaatcct ggaagaccac    5640
aataaacagc tggagtcaca gttacacagg ctaaggcagc tgctggagca accccaggca    5700
gaggccaaag tgaatggcac aacggtgtcc tctccttcta cctctctaca gaggtccgac    5760
agcagtcagc ctatgctgct ccgagtggtt ggcagtcaaa cttcggactc catgggtgag    5820
```

```
gaagatcttc tcagtcctcc ccaggacaca agcacagggt tagaggaggt gatggagcaa      5880
ctcaacaact ccttccctag ttcaagagga agaaatacccc ctggaaagcc aatgagagag      5940
gacacaatgt ag                                                          5952

<210> SEQ ID NO 2
<211> LENGTH: 28
<212> TYPE: DNA
<213> ORGANISM: Artificial Sequence
<220> FEATURE:
<223> OTHER INFORMATION: DnaB intein primer 1

<400> SEQUENCE: 2
ctctagaagg ctgcatcagt ggagatag                                           28

<210> SEQ ID NO 3
<211> LENGTH: 36
<212> TYPE: DNA
<213> ORGANISM: Artificial Sequence
<220> FEATURE:
<223> OTHER INFORMATION: DnaB intein primer 2

<400> SEQUENCE: 3
ctgcgtcgtt cgaattatgg acaatgatgt cattgg                                  36

<210> SEQ ID NO 4
<211> LENGTH: 484
<212> TYPE: DNA
<213> ORGANISM: Artificial Sequence
<220> FEATURE:
<223> OTHER INFORMATION: DnaB intein cassette sequence

<400> SEQUENCE: 4
tgcatcagtg gagatagttt gatcagcttg gcgagcacag gaaaaagagt ttctattaaa        60
gatttgttag atgaaaaaga ttttgaaata tgggcaatta atgaacagac gatgaagcta       120
gaatcagcta aagttagtcg tgtattttgt actggcaaaa agctagttta tattttaaaa       180
actcgactag gtagaactat caaggcaaca gcaaatcata gattttttaac tattgatggt      240 tggaaaagat tagatgagct atcttttaaaa gagcatattg ctctaccccg taaactagaa      300
agctcctctt tacaattata atgaggaggt ttaaaatatg tcaccagaaa tagaaaagtt       360
gtctcagagt gatatttact gggactccat cgtttctatt acggagactg gagtcgaaga       420 ggttttttgat ttgactgtgc caggaccaca taactttgtc gccaatgaca tcattgtcca      480
taat                                                                   484

<210> SEQ ID NO 5
<211> LENGTH: 22
<212> TYPE: DNA
<213> ORGANISM: Artificial Sequence
<220> FEATURE:
<223> OTHER INFORMATION: Ribosome-binding Linker

<400> SEQUENCE: 5
taatgaggag gtttaaaata tg                                                 22

<210> SEQ ID NO 6
<211> LENGTH: 612
<212> TYPE: DNA
<213> ORGANISM: Artificial Sequence
<220> FEATURE:
<223> OTHER INFORMATION: DnaE intein cassette sequence
```

```
<400> SEQUENCE: 6
ttggccctga aacttcttcg cgattattgc ctcagttttg gcaccgaaat tttaaccgtt      60
gagtacggcc cattgcccat tggcaaaatt gtgagtgaag aaattaattg ttctgtgtac     120
agtgttgatc cagaagggag agtttacacc caggcgatcg cccaatggca tgaccgggga     180
gagcaggaag tattggaata tgaattggaa gatggttcag taatccgagc tacctctgac     240
caccgctttt taaccaccga ttatcaactg ttggcgatcg aagaaatttt tgctaggcaa     300
ctggacttgt tgactttaga aaatattaag caaactgaag aagctcttga caaccatcgt     360
cttccctttc cattacttga cgccggaggt taatcaacat atgacatgga tagtttctaa     420
tttaattaat cagcatcaaa aaatccctca aggcttcaca ataatccctg ttgttatggt     480
taaagttatc ggtcgtcgtt ccctcggagt gcaaagaata tttgatattg gtcttcccca     540
agaccataat tttctgctag ccaatggggc gatcgccgcc aattccgcgg atgataccag     600
aaaagtccac at                                                        612

<210> SEQ ID NO 7
<211> LENGTH: 35
<212> TYPE: DNA
<213> ORGANISM: Artificial Sequence
<220> FEATURE:
<223> OTHER INFORMATION: H-62 PCR primer

<400> SEQUENCE: 7
cgcgcagcgg ccgcactttt caaaatgctt tggtg                                35

<210> SEQ ID NO 8
<211> LENGTH: 35
<212> TYPE: DNA
<213> ORGANISM: Artificial Sequence
<220> FEATURE:
<223> OTHER INFORMATION: H-63 PCR primer

<400> SEQUENCE: 8
gctcgcgtcg actacaattg taaagaggag ctttc                                35

<210> SEQ ID NO 9
<211> LENGTH: 43
<212> TYPE: DNA
<213> ORGANISM: Artificial Sequence
<220> FEATURE:
<223> OTHER INFORMATION: H-64 PCR primer

<400> SEQUENCE: 9
gcgcagcggc cgcttttcaa aatgcaattg tcaccagaaa tag                       43

<210> SEQ ID NO 10
<211> LENGTH: 35
<212> TYPE: DNA
<213> ORGANISM: Artificial Sequence
<220> FEATURE:
<223> OTHER INFORMATION: H-65 PCR primer

<400> SEQUENCE: 10
cgcacgcgtc gactacattg tgtcctctct cattg                                35

<210> SEQ ID NO 11
<211> LENGTH: 60
<212> TYPE: DNA
<213> ORGANISM: Artificial Sequence
<220> FEATURE:
<223> OTHER INFORMATION: pXX-N2 5' junction
```

```
<400> SEQUENCE: 11
gcggccgcac ttttcaaaat gctttggtgg aagaagtag aggactgtta tgaaagagaa    60

<210> SEQ ID NO 12
<211> LENGTH: 362
<212> TYPE: DNA
<213> ORGANISM: Artificial Sequence
<220> FEATURE:
<223> OTHER INFORMATION: pXX-N2 3' junction

<400> SEQUENCE: 12 gaaacagcc aaaaaatcct gagatctcta gaaggctgca tcagtggaga tagtttgatc    60
agcttggcga gcacaggaaa aagagtttct attaaagatt tgttagatga aaagattttt   120
gaaatatggg caattaatga acagacgatg aagctagaat cagctaaagt tagtcgtgta   180
ttttgtactg gcaaaaagct agtttatatt ctaaaaactc gactaggtag aactatcaag   240
gcaacagcaa atcatagatt tttaactatt gatggttgga aaagattaga tgagctatct   300
ttaaaagagc atattgctct accccgtaaa ctagaaagct cctctttaca attgtagtcg   360
ac                                                                  362

<210> SEQ ID NO 13
<211> LENGTH: 238
<212> TYPE: DNA
<213> ORGANISM: Artificial Sequence
<220> FEATURE:
<223> OTHER INFORMATION: pXX-C2 5' junction

<400> SEQUENCE: 13
gcggccgctt ttcaaaatgc aattgtcacc agaaatagaa aagttgtctc agagtgatat    60
ttactgggac tccatcgttt ctattacgga gactggagtc gaagaggttt ttgatttgac   120
tgtgccagga ccacataact tgtcgccaa tgacatcatt gtccataatt cggacgacgc    180
agtactgtta caaagacgtt tggataacat gaacttcaag tggagtgaac ttcggaaa    238

<210> SEQ ID NO 14
<211> LENGTH: 20
<212> TYPE: DNA
<213> ORGANISM: Artificial Sequence
<220> FEATURE:
<223> OTHER INFORMATION: pXX-C2 3' junction

<400> SEQUENCE: 14
gaggacacaa tgtagtcgac                                                20

<210> SEQ ID NO 15
<211> LENGTH: 60
<212> TYPE: DNA
<213> ORGANISM: Artificial Sequence
<220> FEATURE:
<223> OTHER INFORMATION: pXX-N4 5' junction

<400> SEQUENCE: 15
gcggccgcac ttttcaaaat gctttggtgg aagaagtag aggactgtta tgaaagagaa    60

<210> SEQ ID NO 16
<211> LENGTH: 422
<212> TYPE: DNA
<213> ORGANISM: Artificial Sequence
<220> FEATURE:
<223> OTHER INFORMATION: pXX-N4 3' junction
```

<400> SEQUENCE: 16

```
gtagatgtgg caaatgactt ggccctgaaa cttcttcgcg attattgcct cagttttggc      60
accgaaattt taaccgttga gtacggccca ttgcccattg caaaattgt gagtgaagaa      120
attaattgtt ctgtgtacag tgttgatcca gaagggagag tttacaccca ggcgatcgcc    180
caatggcatg accggggaga gcaggaagta ttggaatatg aattggaaga tggttcagta    240
atccgagcta cctctgacca ccgcttttta accaccgatt atcaactgtt ggcgatcgaa    300
gaaattttg ctaggcaact ggacttgttg actttagaaa atattaagca aactgaagaa     360
gctcttgaca accatcgtct tccctttcca ttacttgacg ctggaacaat aaatagtcg    420
ac                                                                   422
```

<210> SEQ ID NO 17
<211> LENGTH: 178
<212> TYPE: DNA
<213> ORGANISM: Artificial Sequence
<220> FEATURE:
<223> OTHER INFORMATION: pXX-C4 5' junction

<400> SEQUENCE: 17

```
gcggccgctt ttcaaaatgg ttaaagttat cggtcgtcgt tccctcggag tgcaaagaat    60
atttgatatt ggtcttcccc aagaccataa ttttctgcta gccaatgggg cgatcgccgc    120
caattccgcg gatgatacca gaaaagtcca catgataaca gagaatatca atgcctct      178
```

<210> SEQ ID NO 18
<211> LENGTH: 26
<212> TYPE: DNA
<213> ORGANISM: Artificial Sequence
<220> FEATURE:
<223> OTHER INFORMATION: pXX-C4 3' junction

<400> SEQUENCE: 18

```
atgagagagg acacaatgta gtcgac                                          26
```

<210> SEQ ID NO 19
<211> LENGTH: 20
<212> TYPE: PRT
<213> ORGANISM: Artificial Sequence
<220> FEATURE:
<223> OTHER INFORMATION: pXX-N2 dystrophin-intein peptide junction

<400> SEQUENCE: 19

```
Ser Gln Lys Ile Leu Arg Ser Leu Glu Gly Cys Ile Ser Gly Asp Ser
1               5                   10                  15

Leu Ile Ser Leu
            20
```

<210> SEQ ID NO 20
<211> LENGTH: 20
<212> TYPE: PRT
<213> ORGANISM: Artificial Sequence
<220> FEATURE:
<223> OTHER INFORMATION: pXX-C2 dystrophin-intein peptide junction

<400> SEQUENCE: 20

```
Phe Val Ala Asn Asp Ile Ile Val His Asn Ser Asp Asp Ala Val Leu
1               5                   10                  15

Leu Gln Arg Arg
            20
```

-continued

```
<210> SEQ ID NO 21
<211> LENGTH: 20
<212> TYPE: PRT
<213> ORGANISM: Artificial Sequence
<220> FEATURE:
<223> OTHER INFORMATION: pXX-N4 dystrophin-intein peptide junction

<400> SEQUENCE: 21

Asp Leu Ala Leu Lys Leu Leu Arg Asp Tyr Cys Leu Ser Phe Gly Thr
1               5                   10                  15

Glu Ile Leu Thr
            20

<210> SEQ ID NO 22
<211> LENGTH: 20
<212> TYPE: PRT
<213> ORGANISM: Artificial Sequence
<220> FEATURE:
<223> OTHER INFORMATION: pXX-C4 dystrophin-intein peptide junction

<400> SEQUENCE: 22

Leu Leu Ala Asn Gly Ala Ile Ala Ala Asn Ser Ala Asp Asp Thr Arg
1               5                   10                  15

Lys Val His Met
            20
```

METHOD AND VECTOR FOR PRODUCING AND TRANSFERRING TRANS-SPLICED PEPTIDES

CROSS REFERENCE TO RELATED APPLICATIONS

This application claims the benefit of U.S. Provisional Application No. 60/159,868, filed Oct. 15, 1999.

STATEMENT REGARDING FEDERALLY SPONSORED RESEARCH AND DEVELOPMENT

Not applicable.

BACKGROUND

1. Technical Field

Disclosed are methods for protein trans-splicing, use of trans-spliced proteins in gene therapies and gene therapy vectors that encode proteins that trans-splice. In particular, a method for trans-splicing dystrophin and use in gene therapies of recombinant Adeno-Associated Virus (rAAV) particles that encode trans-spliced dystrophin.

2. Description of the Related Art

Protein splicing elements, protein introns, were first discovered in yeast (Kane, P. M., Yamashiro, C. T., Wolczyk, D. F., Neff, N., Goebl, M., and Stevens, T. H. (1990), Protein splicing converts the yeast TFP1 gene product to the 69-kD subunit of the vacuolar H(+)-adenosine triphosphatase, *Science* 250, 651–657, incorporated herein by reference). Four years later, after six more protein introns had been characterized, they were renamed "inteins" (Perler, F. B., Davis, E. O., Dean, G. E., Gimble, F. S., Jack, W. E., Neff, N., Noren, C. J., Thorner, J., and Belfort, M. (1994), Protein splicing elements: inteins and exteins—a definition of terms and recommended nomenclature, *Nucleic Acids Res.* 22, 1125–1127, incorporated herein by reference). Over 100 inteins have since been found in various precursor (host) proteins in a variety of bacterial, archaebacterial and eukaryotic organisms. An intein is defined as a protein sequence which is embedded in-frame within a precursor protein sequence and which is excised during a maturation process called protein splicing. Protein splicing is a post-translational event involving precise excision of the intein sequence and concomitant ligation of the flanking sequences (N- and C-exteins) by a normal peptide bond.

The chemical mechanism of protein splicing was proposed by several groups in 1993 (Wallace, C. J. (1993), The curious case of protein splicing: mechanistic insights suggested by protein semisynthesis, *Protein Sci.* 2, 697–705; Cooper, A. A., Chen, Y. J., Lindorfer, M. A., and Stevens, T. H. (1993), Protein splicing of the yeast TFP1 intervening protein sequence: a model for self-excision, *EMBO J.* 12, 2575–2583; Xu, M.-Q., Southworth, M. W., Mersha, F. B., Hornstra, L. J., and Perler, F. B. (1993), In vitro protein splicing of purified precursor and the identification of a branched intermediate, *Cell* 75, 1371–1377, both of which are incorporated herein by reference) and has since been supported and refined by experimental data (Xu, M.-Q., Comb, D. G., Paulus, H., Noren, C. J., Shao, Y., and Perler, F. B. (1994), Protein splicing: an analysis of the branched intermediate and its resolution by succinimide formation, *EMBO J.* 13, 5517–5522; Xu, M.-Q. and Perler, F. B, (1996), The mechanism of protein splicing and its modulation by mutation, *EMBO J.* 15, 5146–5153; both of which are incorporated herein by reference). Briefly, a typical intein folds upon itself, bringing the upstream and downstream splice junctions together to form an active center. Splicing involves an N—S or an N—O acyl shift at the splice sites, formation of a branched intermediate, and cyclization of an invariant Asn residue at the C-terminus of the intein to form succinimide, leading to excision of the intein and ligation of the exteins. Amino acid residues that participate directly in the splicing reaction include a nucleophilic amino acid (Cys or Ser), both at the beginning of the intein sequence and at the beginning of the C-extein sequence (Cys, Ser, or Thr), an internal His, and an Asn at the end of the intein sequence. Practical uses of inteins have been made by engineering controllable inteins which undergo controllable protein splicing or cleavage in vitro, including protein trans-splicing by intein fragment reassembly in vitro (Southworth, M. W., Adam, E., Panne, D., Byer, R., Kautz, R., and Perler, F. B. (1998), Control of protein splicing by intein fragment reassembly, *EMBO J.* 17, 918–926; Mills, K. V., Lew, B. M., Jiang, S.-Q., and Paulus, H. (1998), Protein splicing in trans by purified N- and C-terminal fragments of the *Mycobacterium tuberculosis* RecA intein, *Proc. Natl. Acad. Sci. U.S.A.* 95, 3543–3548; both of which are incorporated herein by reference). In vivo protein trans-splicing has also been shown through intein engineering (Shingledecker, K., Jiang, S.-Q., and Paulus, H. (1998), Molecular dissection of the *Mycobacterium tuberculosis* RecA intein: design of a minimal intein of a trans-splicing system involving two intein fragments, *Gene* 207, 187–195; Wu, H., Xu, M.-Q., and Liu, X.-Q (1998b), Protein trans-splicing and functional mini-inteins of a cyanobacterial DnaB intein, *Biochim. Biophys. Acta* 1387, 422–432; each of which are incorporated herein by reference) and the discovery of a naturally occurring trans-splicing intein (Wu, H., Hu, Z., and Liu, X.-Q. (1998a), Protein trans-splicing by a split intein encoded in a split DnaE gene of *synechocystis* sp. PCC6803, *Proc. Natl. Acad. Sci. U.S.A.* 95, 9226–9231; incorporated herein by reference). But until now, no practical use has been described for spontaneous or automatic in vivo protein trans-splicing.

Duchenne muscular dystrophy (DMD) is the most common form of X-linked muscular dystrophy, with a worldwide incidence of one in 3,500 male births (Emery, A. E. H., Duchenne Muscular Dystrophy, Oxford University Press, 1993: 392; incorporated herein by reference). DMD patients appear normal until 3–5 years of age, when they begin to experience progressive muscular weakness, starting with large proximal skeletal muscles. The typical affected individual is wheelchair-bound by the age of 12 and succumbs to cardiac or respiratory failure in the mid to late 20s. Becker muscular dystrophy (BMD) is a milder form with delayed onset and longer life span. Most DMD/BMD cases are transmitted via an unaffected mother (heterozygote), whereas 30% of cases have no previous family history and are considered to be due to a de novo mutation in the germ line of either the mother or her parents.

DMD and BMD are caused by a defective dystrophin protein in a patient's muscle cells (See, Straub, V. and Campbell, K. P. (1997), Muscular dystrophies and the dystrophin-glycoprotein complex, *Curr. Opin. Neurol.* 10, 168–175; Brown, Jr., R. H. (1997), Dystrophin-associated proteins and the muscular dystrophies, *Ann. Rev. Med.* 48, 457–466; Michalak, M. and Opas, M. (1997), Functions of dystrophin and dystrophin associated proteins, *Curr. Opin. Neurol.* 10, 436–442, for recent reviews; each of which are incorporated herein by reference). Dystrophin is a large protein of 3,685 aa and has three structurally distinct regions. The N-terminal region is 136 aa long and forms a globular domain. The C-terminal region is 645 aa long and forms a second globular domain. The central region is a long and rod-like domain that consists of 24 repeats of a triple helical coiled-coil, or of 9 repeats in the smaller, but still functional, Becker form. The N- and C-terminal domains are separated, both in primary sequence and in tertiary structure by the central region. Each repeat is approximately 109 aa long, and there is 10–25% sequence identity between repeats. Each individual repeat is believed to fold independently into a structural module, and neighboring repeats are connected by a short, flexible linker sequence.

Dystrophin is a part of the dystrophin-glycoprotein complex and is thought to function by forming a submembrane lattice which enhances the tensile strength of the muscle membrane and by serving as an anchor for membrane proteins. The human dystrophin gene was identified in 1986 (Monaco, A. P., Neve, R. L., Colletti-Feener, C., Bertelson, C. J., Kurnit, D. M., and Kunkel, L. M. (1986), Isolation of candidate cDNAs for portions of the Duchenne muscular dystrophy gene, Nature 323, 646–650; incorporated herein by reference), the dystrophin protein was identified in 1987 (Hoffman, E. P., Brown, Jr., R. H., and Kunkel, L. M. (1987), Dystrophin: the protein product of the Duchenne muscular dystrophy locus, Cell 51, 919–928; incorporated herein by reference), and the complete dystrophin gene sequence (a 14-kbp cDNA) was cloned and determined by 1988 (Koenig, M., Hoffman, E. P., Bertelson, C. J., Monaco, A. P., Feener, C., and Kunkel, L. M. (1987), Complete cloning of the Duchenne muscular dystrophy (DMD) cDNA and preliminary genomic organization of the DMD gene in normal and affected individuals, Cell 50, 509–517; Koenig, M., Monaco, A. P., and Kunkel, L. M. (1988), The complete sequence of dystrophin predicts a rod-shaped cytoskeletal protein, Cell 53, 219–226; both of which are incorporated herein by reference). Most (over 65%) of the defective dystrophin genes found in DMD and BMD patients exhibit the loss (deletion) of one or more exons, with two deletion hot spots located in the 5' end region and in the central region of the gene, resulting in smaller dystrophin protein. Deletions that cause frameshifts usually lead to DMD and are predicted to produce either a severely truncated dystrophin or no dystrophin at all.

Progression of the DMD and BMD disease cannot yet be slowed by therapeutic treatment. At present glucocorticoid administration is the only drug therapy, but it is only partially effective and has frequent side-effects.

Alternative methods are being sought but have not yet been found. One potential approach is to upregulate the utrophin gene that encodes a close molecular analog of dystrophin (Karpati, G., Gilbert, R., Petrof. B. J., and Nalbantoglu, J. (1997), Gene therapy research for Duchenne and Becker muscular dystrophies, Curr. Opin. Neurol. 10, 430–435; Gramolini, A. O., Angus, L. M., Schaeffer, L., Burton, E. A., Tinsley, J. M., Davies, K. E., Changeux, J. P., and Jasmin, B. J. (1999), Induction of utrophin gene expression by heregulin in skeletal muscle cells: role of the N-box motif and GA binding protein, Proc. Natl. Acad. Sci. U.S.A. 96, 3223–3227; both of which are incorporated herein by reference). However, it is impossible to predict if or when a nontoxic pharmacological agent would be identified to upregulate the human utrophin gene. Myoblast transplantation offers another potential treatment, but its clinical application has several limitations, including immunological problems, low spread and poor survival of the transplanted myoblasts (Qu, Z., Balkir, L., van Duetekon, J. C., Robbins, P. D., Prochnic, R., and Huard, J. (1998), Development of approaches to improve cell survival in myoblast transfer therapy, J. Cell Biol. 142, 1257–1267; Moisset, P. A., Gagnon, Y., Karpati, G., and Tremblay, J. P. (1998a), Expression of human dystrophin following the transplation of genetically modified mdx myoblasts, Gene Ther. 5, 1340–1346; Moisset, P. A., Skuk, D., Asselin, I., Goulet, M., Roy, B., Karpati, G., and Tremblay, J. P. (1998b), Successful transplantation of genetically corrected DMD myoblasts following ex vivo transduction with the dystrophin minigene, Biochem. Biophys. Res. Commun. 247, 94–99; Miller, R. G., Sharma, K. R., Pavlath, G. K., Gussoni, E., Mynhier, M., Lanctot, A. M., Greco, C. M., Steinman, L., and Blau, H. M. (1997), Myoblast implantation in Duchenne muscular dystrophy: the San Francisco study, Muscle Nerve 20, 469–478; each of which are incorporated herein by reference). Another possibility is to convert DMD to BMD by correcting the frameshift mutation in the DMD dystrophin gene at the RNA level (Matsuo, M. (1996), Duchenne/Becker muscular dystrophy: from molecular diagnosis to gene therapy, Brain & Development 18, 167–172; incorporated herein by reference), but the necessary molecular tools remain to be found.

Gene therapy is recognized as the most plausible candidate for an effective therapy for DMD and BMD (reviewed in Karpati et al., 1997). A simple and proven way is to transfer into patient muscle cells a functional dystrophin gene that produces functional dystrophin. The endogenous defective dystrophin gene is harmless in the presence of the transferred functional dystrophin gene because DMD/BMD are recessive. A miniature version of the dystrophin gene, which was isolated from a BMD patient with very mild symptoms (England, S. B., Nicholson, L. V. B., Johnson, M. A., Forrest, S. M., Love, D. R., Zubrzycka-Gaarn, E. E., Bulman, D. E., Harris, J. B., and Davies, K. E. (1990), Very mild muscular dystrophy associated with the deletion of 46% of dystrophin, Nature 343, 180–182; Love, D. R., Flint, T. J., Sally, A. G., Middleton-Price, H. R., and Davies, K. E. (1991), Becker muscular dystrophy patient with a large intragenic dystrophin deletion: implications for functional minigenes and gene therapy, J. Med. Genet. 28, 860–864; both of which are incorporated herein by reference), can be used in the gene transfer. This minigene (6 kbp cDNA) produces a smaller (1,983 aa, 200 kDa) but still functional dystrophin, which is only slightly less effective than the full length dystrophin gene when tested in transgenic mdx mice. In efficiently transduced muscles of mdx mice, loss of force induced by lengthening contractions was alleviated.

Until now adenovirus-based vector has been the most efficient vector for dystrophin gene transfer into muscles when tested on animal models (mdx mouse and dog) at an early age (see, Karpati et al., 1997 for a review). However, adenovirus vectors have several important drawbacks. First, cellular and humoral immunity triggered by leaky expression of adenovirus proteins and input load of adenovirus proteins, respectively, eliminates transduced fibers and may enhance cytotoxic effects. Second, early non-immunological toxic effects reduce muscle force by ~20% and restrict the maximum adenovirus titer that can be used. Third, there is limited uptake of adenovirus into mature muscle fibers (compared to myoblasts), probably due to lack of cell receptors and the basal lamina barrier. Fourth, when directly injected into a limb muscle, adenovirus vector shows a moderate spread (1–3 mm), which necessitates a high concentration of injection sites. Adenovirus vector injected into the systemic venous circulation is mostly expressed in liver. New adenovirus vectors that are under development may partially overcome some of these drawbacks, but progress is limited.

Adeno-associated Virus (AAV) vector has characteristics that overcome the drawbacks associated with adenovirus vector. First, there are no deleterious CTL immune reactions. Second, AAV vector has less non-immunological toxic effects. Third, AAV vector efficiently transduces mature muscle fibers. Fourth, AAV vector can be prepared free of contaminating adenovirus because of the large size difference between the virus particles. Fifth, AAV itself has no known pathogenicity. Sixth, when directly injected into muscle, AAV vector diffuses more broadly and rapidly due to its smaller particle size and due to its ability to bypass myofiber basal laminae and thereby transduce mature muscle cells. In addition, AAV vector can integrate into the host genome, even in quiescent cells, improving the longevity of the transgene.

Recombinant AAV vectors harboring test genes such as LacZ are capable of achieving highly efficient and sustained gene transfer in the mature muscle of immuno-competent animals for more than 1.5 years without detectable toxicity. Vector integration into the host DNA and the lack of CTL response against transduced cells support the potential of rAAV vectors for genetic muscle diseases. Recently, researchers have greatly improved their ability to generate high titer and high quality rAAV. Successes have been reported in using rAAV vectors to deliver numerous reporter genes as well as therapeutic genes for metabolic diseases, including producing secreted therapeutic proteins using muscle as a platform (Li, J. Dressman, D., Tsao, Y. P., Sakamoto, A., Hoffman, E. P., and Xiao, X., rAAv Vector-mediated sarcoglycan gene transfer in a hamster model for limb girdle Muscular Dystrophy, *Gene Therapy* (1999) 6:74–82; Greelish, J. P., Su, L. T., Lankford, E. B., Burkman, J. M., Chen, H., Konig, S. K., Mercier, I. M., Desjardins, P. R., Mitchell, M. A., Zheng, X. G., Leferovich, J., Gao, G. P., Balice-Gordon, R. J., Wilson, J. M., and Stedman, H. H. (1999), Stable restoration of the sarcoglycan complex in dystrophic muscle perfused with histamine and a recombinant adeno-associated viral vector, *Nat. Med.* 5, 439–43; both of which are incorporated herein by reference). Yet using rAAV vector to treat genetic muscle diseases is just beginning to be explored.

The effectiveness of rAAV vectors has been demonstrated in a gene therapy for limb girdle muscular dystrophy (LGMD) 2F, which is caused by mutations in the δ-sarcoglycan (SG) gene. A rAAV vector was used for genetic and biochemical rescue in the Bio 14.6 hamster, a homologous animal model for LGMD 2F (Li et al., 1999). Subsequently, efficient and long-term δ-SG expression was demonstrated, accompanied by nearly complete recovery of physiological function deficits, after a single dose rAAV vector injection into the tibialis anterior (TA) muscle of the dystrophic hamsters. Recombinant AAV vector treatment led to more than 97% recovery in muscle strength for both specific twitch force and specific tetanic force, when compared to the age-matched control. Vector treatment also prevented pathological muscle hypertrophy, and resulted in normal muscle weight and size. Finally, the histopathology of vector treated muscle showed substantial improvement. This is the first evidence of a successful functional rescue of an entire muscle after AAV mediated gene delivery. These results demonstrate the feasibility of in vivo gene therapy for dystrophic patients using rAAV vectors.

Recombinant AAV vector, until now, has been excluded from gene therapy for DMD and BMD because its maximum insert gene size (4.5–4.8 kbp) is smaller than the size of a functional dystrophin gene or minigene. For example, a vector containing the Becker cDNA must accommodate a sequence of about 7 kbps, the 6 kbp coding sequence plus approximately 1 kbp of necessary accessory sequences. A method is therefore desired which solves this problem and allows the use of AAV vector in gene therapy for DMD and BMD and for other therapies which require the transfer of other nucleotide sequences of sizes greater than the packaging limits of a given vector.

SUMMARY

A method is provided that makes use of spontaneous in vivo protein trans-splicing to circumvent packaging limitations of gene therapy vectors, particularly rAAV. The method includes the steps of 1) breaking a gene, for instance the functional dystrophin minigene, into at last two pieces, both of which are smaller than the maximum insert gene size of a transfer vehicle, 2) modifying each piece by operably linking an appropriate fragment of an intein coding sequence and suitable genetic regulatory elements to the dystrophin coding sequences to form extein genes, and 3) transferring each of the two or more extein genes into target cells by using an appropriate vehicle, such as rAAV. The two or more extein genes, once transferred into the same target cell, will produce two or more exteins that will automatically splice together to form a functional dystrophin protein.

More broadly, a method is provided for trans-splicing proteins, including the steps of providing two or more nucleic acids, each encoding and capable of expressing protein fragments to be joined at a junction site by trans-splicing. Preferably, the two or more nucleic acids are produced by severing, at a junction site, a nucleotide sequence encoding a single protein a gene product. Flanking each junction site are nucleotide sequences encoding relative N- and C-extein segments. Relative to each junction site, the 3' end of the nucleic acid encoding the N-extein segment includes, in phase, a sequence encoding an N-terminal portion of a split intein. The 5' end of the nucleic acid encoding the relative C-extein segment having, in phase, a sequence encoding a C-terminal portion of the same split intein. A split intein can be a native split intein or a split intein engineered from a native intein, such as the Ssp DnaE and Ssp DnaB inteins, or an engineered split intein prepared synthetically with reference to known intein consensus sequences and structures.

Three or more protein or peptide sequences can be joined at two or more junction sites. In such a case, a different intein is utilized at each junction site to ensure correct assembly of the protein by preventing cross-splicing of the extein fragments.

Also provided is a nucleic acid including at least one of the above-described extein genes.

In one application, the extein genes are transferred to a recipient, such as a human patient or to an in vitro or ex vivo cell culture. The extein genes are transferred by a vehicle, which is preferably a recombinant virus particle, and most preferably a rAAV particle. The particles can be administered either as a population of individual extein genes, or collectively, as a population of particles representing an extein gene set. The particles can be, therefore, administered as a pharmaceutical composition that minimally includes a nucleic acid encoding one of an extein gene, a vehicle containing a nucleic acid encoding an extein gene, the product of an extein gene or the spliced product of two or more extein gene products, and a suitable excipient. The excipient is chosen as suitable for, and preferably optimal for, a chosen delivery route such as parenteral delivery, including intramuscular delivery, or delivery to an in vitro or ex vivo cell culture. The extein gene pharmaceutical composition, or the trans-spliced product thereof, can be packaged as a kit that includes the pharmaceutical composition packaged within a suitable sealed vessel or container.

In one embodiment, the transferred nucleotide sequences encode human dystrophin, or a functional derivative, homolog or analog thereof and the viral vector is AAV. Recombinant AAV particles include a dystrophin extein gene, including at least one partial coding sequence of the dystrophin gene flanked in phase by a coding sequence of a C- and/or N-terminal portion of an intein and under transcriptional control of a suitable promoter and terminator. When expressed in a cell, along with additional extein genes which represent, collectively, an extein gene set including a full complement of dystrophin extein genes, the extein protein segments assemble to form an intact dystrophin protein. Other well-characterized and promising candidates for use in the methods and compositions described herein are the Factor VIII, dysferlin and ATP binding cassette transporter genes.

BRIEF DESCRIPTION OF THE DRAWINGS

The file of this patent contains at least one drawing executed in color.

FIG. 2 shows the nucleotide sequence of the dystrophin gene (Becker). Splice sites S4 (nt. 2847) and S2 (nt. 3198) SEQ ID NO:1 are indicated in bold.

FIG. 4 shows the nucleotide sequence of the Ssp DnaB intein cassette SEQ ID NO:4 of Example 1.

FIG. 6 shows the nucleotide sequence of the Ssp DnaE intein cassette SEQ ID No: 6 of Example 2.

DETAILED DESCRIPTION

Figure 1:
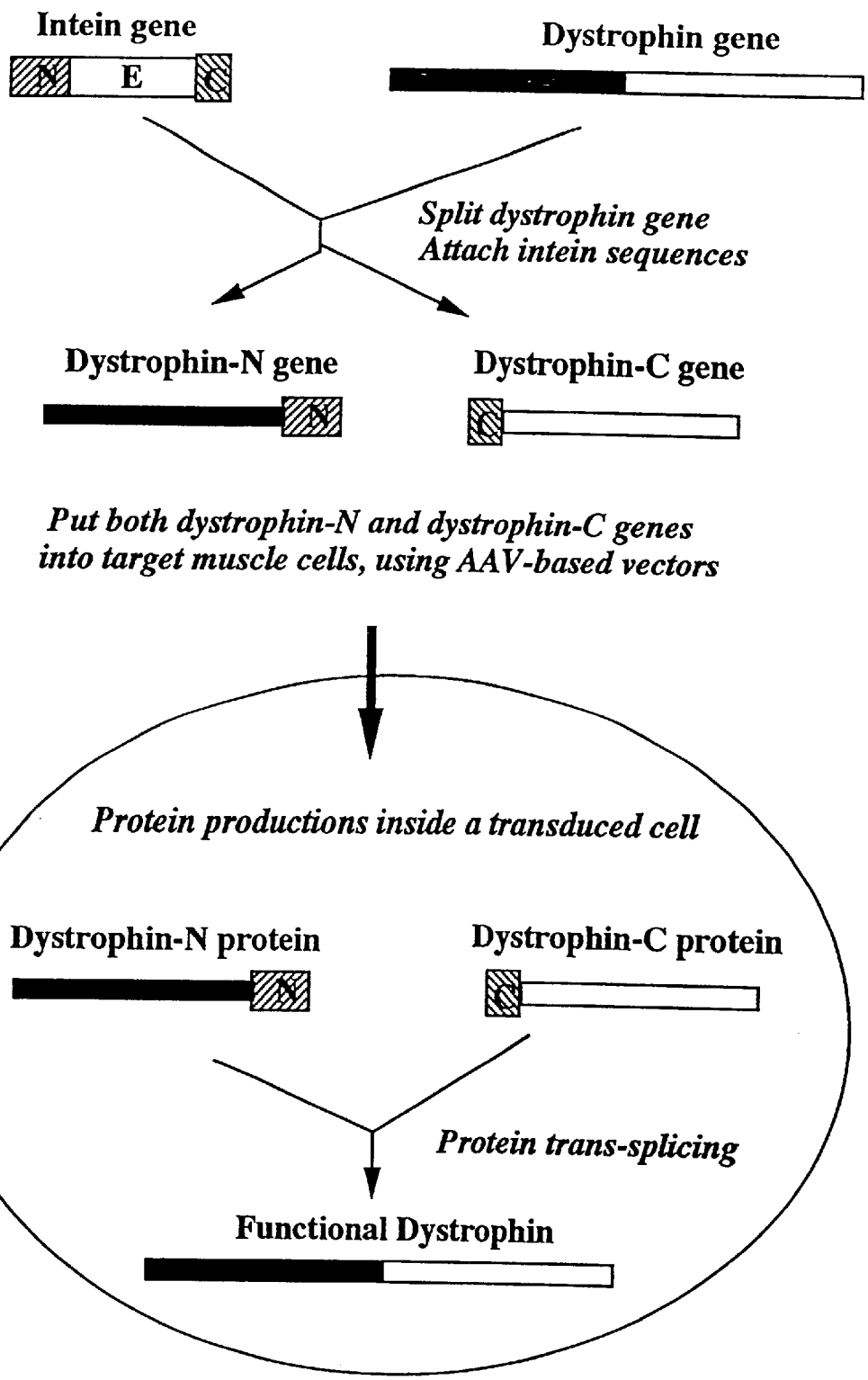
FIG. 1 is a schematic illustration of an embodiment of a method which includes splitting a dystrophin minigene into two pieces, modifying each piece by adding an appropriate piece of an intein sequence, using an AAV vector to transfer the modified gene pieces into target human cells, and production of functional dystrophin through protein trans-splicing in the transduced cell.

Described herein is a method directed to the use of spontaneous, or automatic, protein trans-splicing to join two or more peptides. In one embodiment, among other applications, the trans-splicing is used to circumvent virion packaging size limitations in recombinant virus particles. A recombinant virion's packaging limits may be circumvented by splitting a gene into two or more portions and engineering therefrom extein-encoding nucleic acid segments which include, in phase, co-reacting-split intein-encoding sequences. When expressed, the exteins assemble into a complete protein by trans-splicing of the split intein.

As used herein, the term "vector" means any construct or composition by which the expression, transfer or manipulation of a nucleic acid may be accomplished or facilitated. For example, and without limitation, a "vector" can be a plasmid, a viral nucleic acid, a virus particle, or a liposome, but, as used herein, is typically a plasmid or a viral nucleic acid. "Vehicle" describes any construct, particle or composition that may be used to transfer a nucleic acid, protein or other compound to a recipient cell, organ or organism. For instance, and without limitation, virus particles and liposomes are both "vehicles" as well as "vectors" and are typical vehicles as used herein.

Described is a method for joining two or more peptides at a junction site and applications therefor. The protein sequences can be two contiguous peptides of the same protein, or any two peptides. The peptides to be joined can be engineered and/or prepared as extein peptides wherein the junction site of each peptide abuts split intein sequences which co-react to join the peptides at the junction site. The peptides can be produced in any manner. In a typical embodiment, the extein peptides are produced by recombinant methods. However, the extein peptides also can be prepared synthetically.

In the recombinant methods, genes which express the extein peptides are engineered. In such a method, a first nucleic acid is provided which encodes and is capable of expressing a first peptide in a suitable host cell. The first peptide includes at its C-terminal end an N-terminal portion of a split intein. A second nucleic acid is provided which encodes and is capable of expressing a second peptide in a suitable host cell. The second peptide includes at its N-terminal end a C-terminal portion of the same split intein. The first and second nucleic acids can be provided on the same or on different nucleic acid molecules. A trans-spliced peptide is produced by transferring the first nucleic acid and the second nucleic acid into a suitable host cell under conditions under which the first peptide and the second peptide are expressed and will splice. By "capable of expressing" it is meant that the nucleic acid includes both nucleotides encoding the peptide to be expressed and sufficient genetic regulatory elements, i.e., and without limitation, promoters, enhancers and terminators to form a transcription unit for expression of the peptide. By "expression" or "gene expression," and like words and phrases it is meant the overall process by which the information encoded on a gene or nucleic acid is converted into a protein, or a post-translationally modified version thereof, and/or an observable phenotype.

As stated above, the peptides can be contiguous peptides of a single protein or gene product. In such a method, a nucleic acid is provided which corresponds to a coding region of a gene and which encodes the protein. The coding region of the nucleic acid is severed at one or more junction sites to form two or more nucleic acid portions. Each junction site abuts a 5' coding region and a 3' coding region of the gene. For each junction site, a 3' extein gene and a 5' extein gene are prepared by; 1) attaching to the 3' end of the 5' coding region abutting the junction site a nucleotide sequence encoding a portion of a split intein, to form a nucleic acid encoding a 5' extein; 2) attaching to the 5' end of the 3' coding region abutting the junction site a nucleotide sequence encoding a portion of the split intein which, along with the portion of the split intein attached to the 3' end of the 5' coding region abutting the junction site, comprises a functional split intein, to form a nucleic acid encoding a 3' extein; and 3) preparing one of (i) an extein gene or (ii) both a 5' extein gene and a 3' extein gene by placing the nucleic acids encoding the 5' extein and the 3' extein under control of suitable transcription control sequences for expression of the 5' extein and the 3' extein in a suitable host cell. When the 5' and the 3' exteins are expressed in the cell, they will splice. If there are two or more junction sites, a different split intein can be used at each junction site so that portions of each split intein will not splice with portions of any of the different split inteins. The extein gene(s) can be provided on the same or on different nucleic acid molecules. The protein or gene product is produced by transferring into a suitable host cell the nucleic acid or nucleic acids comprising the extein genes and corresponding to the 5' extein gene and the 3' extein gene for all junction sites and under conditions under which the extein genes are expressed and will splice.

The above-described methods can be used to circumvent packaging limitations in a nucleic acid delivery vehicle for use in a gene therapy. In this embodiment, two or more extein genes are provided on at least two nucleic acids, which are packaged separately in at least two delivery vehicles for delivery into a cell. The nucleic acids including the extein gene(s) can be part of the same or different nucleic acid molecules, so long as the size of the nucleic acid including the extein gene(s) is within the packaging limitations of the vehicle which is to be used to deliver the extein gene(s) to a target cell. A cell is contacted with the delivery vehicles so that the extein genes are transferred into the cell and, when expressed, the expressed product will splice. The nucleic acid of the extein gene(s) can include nucleotide sequences required for packaging of the nucleic acid into a recombinant virus particle.

For each of the embodiments in which the extein peptides are produced by recombinant methods, suitable transcriptional control sequences (i.e., without limitation, promoters, enhancers and terminators) may be used. Promoters can be, for example and without limitation, constitutive or semi-constitutive (i.e., CMV and RSV promoters) or tissue-specific promoters (i.e., a muscle creatinine kinase (MCK) promoter).

Thus, as described above, two or more extein genes can be formed, coding for adjacent segments of the trans-spliced end-product protein. Extein genes may be without limitation, mono-, bi-, di-, or multi-cistronic, depending upon the particular application of this embodiment. Extein genes may collectively comprise an extein gene set, which refers to two or more extein genes which combine to encode trans-splicing exteins which splice to form a complete desired protein or peptide product. Each of the two or more extein genes can be incorporated into a separate vehicle, i.e., a virus particle, and can be transferred into a recipient cell. When an extein gene set is expressed in the same cell, the above-described extein genes encode fragments of the protein which will trans-splice to form a complete protein.

In a therapeutic context, each of the two or more extein genes, each encoding a protein/intein segment which collectively form an extein set, can be transferred to a target cell by a vehicle, such as a recombinant AAV particle. The two or more extein genes can be transferred in sufficient multiplicity, or in a sufficient manner, to ensure that a complete extein gene set, i.e., at least one copy of each of the two or more extein genes of the extein gene set, is transferred to each cell targeted by the therapy. Co-transferring two genes via separate AAV vectors into the same target cell has been shown previously with other genes. In any case, the multiplicity of each extein gene-containing virus particle can be adjusted to optimize production of trans-spliced protein. Expression of the extein gene set in the target cell results in assembly of the complete protein in the target cell.

When extein genes are used to produce the extein peptides, the extein genes are encoded by a nucleic acid (typically single or double stranded RNA or DNA) incorporated into a vector which can be transferred to a recipient cell or organism by a vehicle which is, preferably, a recombinant virion and, most preferably an AAV particle. However, AAV is but one of many applicable gene therapy vectors in which packaging size is limited and dystrophin is but one example of a protein which can be broken into two or more segments so that it can be transferred by a given viral vector.

There are many candidate split inteins which can be used in the trans-splicing methods described herein. Important is the ability of the split intein to trans-splice. To date, only one split intein is known to exist in nature and is known to have a trans-splicing function. This split intein (Ssp DnaE intein) was found in a DNA polymerase protein (DnaE) of a cyanobacterium (Synechocystis sp., a photosynthetic bacterium). This DnaE protein is produced from two separate genes (i.e., half-genes) named dnaE-n and dnaE-c, respectively. The dnaE-n gene produces a half-protein consisting of the N-terminal half of DnaE followed by a 123 aa intein sequence. The dnaE-c gene produces a half-protein consisting of a 36 aa intein sequence followed by the C-terminal half of DnaE. The two intein sequences together constitute a complete split intein that is capable of protein trans-splicing, which converts the two half-proteins into a complete, continuous, and functional DnaE protein. Besides this naturally occurring split intein, a new split intein has been engineered from a conventional intein and demonstrated its protein trans-splicing function. The Ssp DnaB intein, a conventional intein, also from cyanobacterium, was converted into a split intein by first deleting its endonuclease domain and then splitting its remaining sequence (protein splicing domain) into a 100 aa N-terminal portion and a 50 aa C-terminal portion. This engineered split intein was used herein to successfully trans-splice two dystrophin fragments. Split intein sequences can be engineered from conventional inteins, as described, or, in view of known intein consensus structures and sequences, prepared synthetically by DNA synthesis methods to create a nucleic acid encoding split intein.

A listing of candidate inteins can be found in The New England Biolabs Intein Database (Perler, F. B. (1999), InBase, the New England Biolabs intein database, *Nucleic Acids Res.* 27:346–347, incorporated herein by reference). Candidate inteins can be assayed readily for trans-splicing activity in the spirit of the present disclosure according to the protocols established herein with regard to the Ssp DnaB intein. Common intein structures include: C-terminal splice domains, which are typically about 50 aa; N-terminal splice domains, which are typically about 100 aa, and a linker or homing endonuclease domain therebetween. Typically, in order to minimize the size of the extein genes and to prevent extraneous enzymatic reactions, the linker or homing endonuclease sequences may be removed.

However, other protein structures can serve as candidate inteins. For instance, it is known that although certain inteins share little sequence homology, their three-dimensional structure is quite similar. Thus, protein structures which share three-dimensional structures with inteins, as well as functionality, will be equally suitable as candidate inteins. For instance, in view of the strong similarities between intein structures and the beta-strand structure of the *Drosphila hedgehog* protein autoprocessing domain (the HINT module), this domain, as well as other HINT domains, are believed to be equally suited as candidate inteins. Protein splicing (trans- or cis-) is an autocatalytic event and does not require any cellular machinery other than the intein itself (reviewed in Perler, F. B. (1998), Protein Splicing of inteins and Hedgehog autoproteolysis: structure, function, and evolution, *Cell* 92, 1–4). The typical intein sequence (split or continuous) contains all the necessary structural and catalytic information for splicing. An intein, regardless of its bacterial or eukaryotic cell origin, can function in other cells and in test tubes (in vitro). Protein splicing (trans- or cis-) is also independent of the nature of the host protein (N- and C-exteins). An intein from one host protein can still function when placed in a different host protein or in a different location of the same host protein. The only required amino acid residue in a host protein is a nucleophilic residue (Ser, Cys, or Thr) located immediately after the intein sequence. Protein splicing (trans- or cis-) is accurate and specific, as have been demonstrated numerous times with various inteins and host proteins (reviewed in Perler, F. B., 1998). The intein structure and the protein splicing mechanism ensure that the splicing is a precise and seamless joining of the host protein sequences (the N- and C-exteins) by a normal peptide bond. In the case of split intein, the two intein parts recognize each other, reassemble, and function in a precise and specific manner. They only splice together the two proteins (peptide fragments, exteins) that are linked to them by a peptide bond. This has been demonstrated on many occasions by directly sequencing proteins that were produced through cis or trans protein splicing (e.g., Wu et al., 1998a).

The efficiency of protein splicing varies with different inteins and host proteins. In the case of protein cis-splicing, some inteins work so fast that the precursor (unspliced) proteins escape detection, while others are sufficiently slow to accumulate detectable levels of the precursor (unspliced) protein. In the case of protein trans-splicing when tested in *E. coli* cells, the Ssp DnaB intein and the Ssp DnaE intein showed from 50% to nearly 100% complete conversion of the half-proteins to the spliced protein. Various structural and biochemical studies suggest that the efficiency of protein splicing is affected by the following factors: 1) some inteins are naturally more efficient than others; 2) the site of intein insertion may affect splicing, because amino acid residues immediately next to the splice junctions may influence the intein active center; and 3) for trans-splicing, the efficiency may be dependent to a large degree on how strongly the two half-proteins bind each other to allow the intein parts to re-assemble.

Dystrophin, because of its structure, described above, is particularly suited for production by protein trans-splicing. One consideration in producing a protein through protein trans-splicing is avoiding misfolding of the half-proteins prior to splicing. The dystrophin gene can be split into two half-genes at locations corresponding to flexible linker sequences in the central rod domain. The dystrophin structure predicts that each of the two half-proteins will fold independently and properly, like they normally do in a complete dystrophin. This minimizes the risk of mis-folding of the half-proteins before protein trans-splicing, which ensures correct structure and function of the dystrophin after its formation by trans-splicing. Also, the flexible linker sequences have several nucleophilic amino acid residues (Ser, Cys, or Thr) that are needed at the intein insertion site.

As used herein, any derivative, analog, or homolog of dystrophin, which retains dystrophin functionality capable of correcting DMD or BMD is considered to be "dystrophin." Therefore, without limitation, native dystrophin, alleles thereof, engineered versions thereof, nonhuman analogs or homologs thereof or mutants thereof containing insertions, deletions, replacements and modifications, including post translational modifications (collectively "functional derivatives" of dystrophin) are considered to be "dystrophin," so long as dystrophin activity is retained.

Other genes that are well-characterized and that are particularly suitable for use in the methods and compositions described herein are the Factor VIII, dysferlin and ATP binding cassette transporter genes. Defects in the Factor VIII gene product (GenBank Accession No. E00527) are found in patients with hemophilia A. Defects in the dysferlin gene product (GenBank Accession No. NM 003494) are found in patients with LGMD 2B and Miyoshi myopathy. Defects in the ATP binding cassette transporter gene product (GenBank Accession No. NM 007168) are linked to defects in cholesterol metabolism, and therefore, heart disease.

The method for circumventing packaging limitations of gene therapy (gene delivery) vectors and vehicles described herein is equally applicable to any viral vector/vehicle system, or any vector/vehicle system, which poses packaging imitations. AAV is a particularly suitable viral vector/ vehicle due to its superior characteristics as a gene therapy vector, as described above. Examples of other suitable viral vectors include without limitation Adenovirus and Retrovirus vectors which each include their own respective packaging limitations. Although other viral vectors, such as Vaccinia virus and Herpes virus, have very large packaging limitations (for example, 20 kb for Herpes Simplex Virus), the protein trans-splicing methods are equally applicable to these vectors, if necessary.

Although the method for splitting a protein for delivery is applicable primarily to overcoming packaging limitations of viral vectors or vehicles, it is equally applicable to any situation where a gene must be divided into two parts and delivered via any vehicle. As described above, a small gene may require large accessory sequences (e.g., promoters) for proper function and, therefore, must be divided when transferred by a vehicle with strict packaging limitations. However, the disclosed methods also can be utilized as a method for expressing proteins which either have nucleic acids which are difficult to clone as a complete coding sequence due to difficult secondary structures, or proteins, which, if translated as a whole, would not fold correctly.

In one embodiment, the individual extein genes that, together, form an extein gene set, are inserted into AAV vector DNA, packaged into AAV virions, and delivered to target recipient cells. In the data presented below, a dystrophin gene is split into N and a C portions, which are operably linked to co-reacting split intein portions so that the dystrophin N and C portions trans-splice. By splitting the dystrophin gene into two roughly equal portions, the N and C dystrophin extein genes fit within the packaging limitations of AAV particles. The general method for producing the AAV borne N and C dystrophin extein genes is shown schematically in FIG. 1.

Packaging of the extein genes into recombinant AAV particles may be achieved by a number of methods well-known in the art (Xiao, X., J. Li, and R. J. Samulski (1998), Production of high-titer recombinant adeno-associated virus vectors in the absence of helper adenovirus, *Journal of Virology* 72:2224–32; Snyder, R., X. Xiao, and R. J. Samulski, 1996. Production of recombinant adeno-associated viral vectors, p. 12.1.1–12.2.23, In N. Dracopoli and J. Haines and B. Krof and D. Moir and C. Seidman and J. S. Seidman, D. (ed.), Current protocols in Human Genetics, John Wiley & Sons Ltd., New York; both of which are incorporated herein by reference). Typically, once a candidate protein is identified and nucleic acid encoding the protein is severed into multiple segments, nucleic acids encoding appropriate portions of inteins are operably linked to the segments. Appropriate promoters and terminator sequences, as well as other transcriptional control sequences, may be operably linked to each segment in the direction of transcription, to form an extein gene. Each extein gene is typically ligated into a plasmid containing AAV inverted terminal repeats (ITRs) so that the extein gene is flanked by the ITRs.

Choice of AAV vector nucleic acids includes nucleic acids derived from any AAV serotype and modified or synthetic versions thereof. Recombinant AAV (rAAV) vector nucleic acids include, at a minimum and in addition to non-AAV sequences (i.e., the extein gene), those sequences of wild type AAV, or modified versions thereof, which typically allow for: packaging of the AAV genome into a rAAV particle; delivery of the rAAV genome to a target cell; second strand synthesis of the rAAV genome within the target cell; and expression of a gene or genes encoded by the rAAV genome. The rAAV genome may also include sequences which allow integration of the rAAV genome into the target cell genome if AAV Rep proteins are present in the target cell. These viral sequences are typically found in the AAV ITRs and are herein collectively referred to as ITR sequences even though additional wild-type AAV sequences might also be included in the vector nucleic acid. Examples of suitable plasmid vectors for producing rAAV are pSSV9, pTR-UF1 and pXX-UF1 (Li et al., 1999).

The above-described rAAV vector nucleic acids also include synthetically derived ITR sequences which mimic wild-type AAV ITRs in their use as rAAV vectors and are considered to be "ITRs." One example of such a synthetic ITR is, without limitation, the "double D" sequence described in U.S. Pat. No. 5,869,305, which is incorporated herein by reference. It is understood that the two ITR sequences flanking the inserted intein gene need not be the same and can be derived from the different viral serotypes, modified version thereof or synthetic ITRs.

One preferred site of delivery of rAAV particles is muscle cells or muscle tissue. Muscle cells and/or tissue includes all types of muscle cells and progenitors thereof. Examples of administration and expression of rAAV particles in muscle cells can be found in PCT Publication WO/9640272, U.S. Pat. No. 5,858,351, both of which are incorporated herein by reference, and Li et al., 1999). Generally, skeletal muscle is a preferred site for administration of rAAV particles because it is not a vital organ and it is easy to access. When the protein to be expressed is dystrophin it is preferred that the rAAV particles are administered to muscle.

Use of muscle-specific promoters, such as the muscle creatine kinase promoter, (MCK), as opposed to semi or fully constitutive promoters such as the CMV and RSV promoters, is preferred when the rAAV is administered intramuscularly to target expression of the protein to muscle cells and tissue and to prevent expression in other tissues, or in the host cell in which the recombinant virus particles are prepared, which in the case of the dystrophin gene, and most likely in other protein delivery systems, would be undesirable. In the case of delivery of dystrophin by rAAV particles, rAAV may be administered to each muscle or systemically. If the promoter were not muscle-specific, it is likely that this broad dissemination of rAAV would result in transformation of a large number of non-muscle cells in which expression of the dystrophin gene is not desirable and might be harmful. The MCK promoter is 1.2 kbp in size and smaller versions of this promoter have become available. Since dystrophin can be broken into two 3.5 kbp fragments, the two resultant extein genes would fall within the 5 kbp packaging limitations of rAAV particles.

Nucleic acids, recombinant virus particles or trans-spliced products described herein may be contacted in vitro or ex vivo with cells or administered in vivo in a pharmaceutical composition. In any case, the nucleic acid, virus particle or peptide product is contacted or administered as a composition that includes other ingredients that facilitate the given delivery method. These other ingredients, whether inert or active, for example and without limitation, in preserving or delivering the nucleic acids, virus particles or peptide products, are referred to collectively as "excipients." Specific examples of excipients include, without limitation, buffers, salts, adjuvants, proteins or peptides, polymeric materials, dyes and mono-, oligo- and poly-saccharides. Solutions containing the nucleic acids, virus particles or peptides may be stored or packaged in sealed vessels or syringes and may form part of a kit that includes other items, such as instructional pamphlets, to facilitate distribution of and end-use of the nucleic acids, virus particles or peptides.

EXAMPLE 1

The method for using an intein to splice together two dystrophin pieces was first developed and tested in *E. coli* cells. A 1.26 kbp EcoRI-XhoI fragment from the central rod domain of dystrophin (Becker form), beginning in repeat 5 and ending in repeat 9, was used in this initial test (corresponding to nucleotides 2561–3817 of the Becker form of dystrophin coding sequence (Koenig et al., 1988). The sequence of the dystrophin gene (Becker form), as used in the experiments described hereinbelow, is provided in FIG. 2 (SEQ ID NO: 1).

Figure 3:
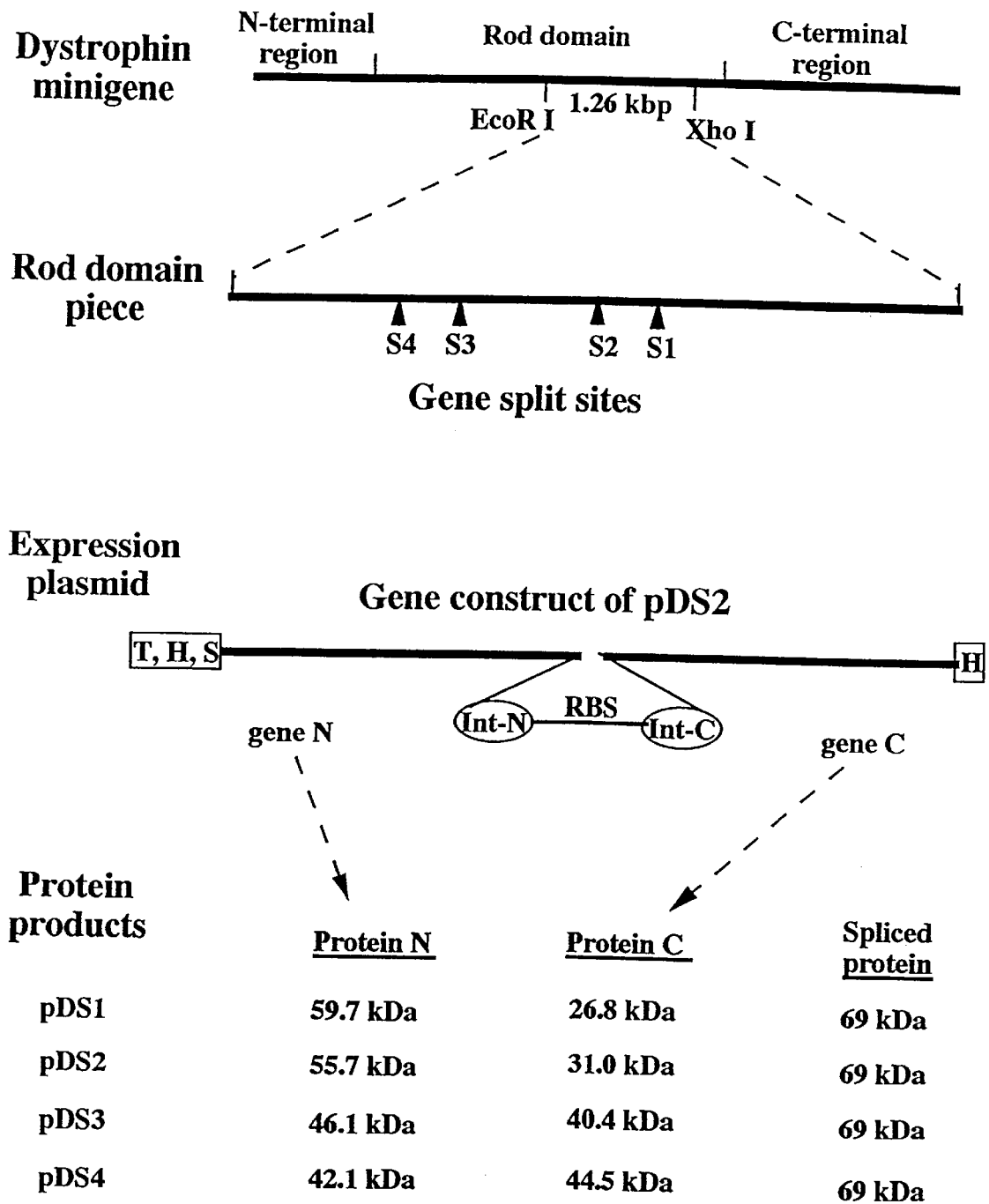
FIG. 3 is a diagrammatic outline of the initial test of the method of Example 1.

The coding sequence of the 1.26 kbp dystrophin fragment was inserted in the expression plasmid vector pET-32b(+) (commercially available from Novagen, Inc. of Madison, Wis.), split at a specific location described herein, and modified by adding specific intein sequences, as shown in FIG. 3.

The intein sequences are provided in a split intein cassette, engineered from the Ssp DnaB intein. The intein cassette was prepared by PCR using the plasmid pMST-split (Wu et al. 1998b) as a template and the oligonucleotides 5'-ctctagaaggctgcatcagtggagatag-3' (SEQ ID NO: 2) and 5'-ctgcgtcgttcgaattatggacaatgatgtcattgg-3' (SEQ ID NO: 3) as PCR primers. The full sequence of the intein cassette is shown in FIG. 4 (SEQ ID NO: 4). Four locations were tested for splitting the dystrophin gene and inserting intein sequences. These sites, designated S1 to S4, correspond to insertion sites immediately after nucleotides 3300, 3198, 2952 and 2847, respectively, of the dystrophin coding sequence (Becker form)(SEQ ID NO: 1). These locations were selected based on several considerations: 1) the insertion site breaks the dystropin minigene into two approximately equal halves; 2) there is a nucleophilic amino acid residue (Ser, Cys, or Thr) immediately after the intein insertion site; and 3) the insertion site is in a flexible linker region of the coiled-coil and does not disrupt the alpha helices. Intein sequences for modifying the split dystrophin genes were prepared as an intein cassette from the Ssp DnaB intein. The intein cassette includes coding sequences for the N-terminal 100 aa and the C-terminal 48 aa of the intein, which were connected with a synthetic ribosome-binding linker sequence 5'-taatgaggaggtttaaaatatg-3' (SEQ ID NO: 5).

This intein cassette was inserted into the dystrophin coding sequence at each of the 4 above-described locations, producing plasmids pDS1 through pDS4, respectively. Each of these plasmids has a two-gene operon, including extein genes, named gene N and gene C, respectively. Gene N encodes protein N consisting of an N-terminal piece of the dystrophin sequence that is modified at its C-terminus by the intein N-terminal sequence (Int-N) and at its N-terminus by tag sequences (T, H, and S). Gene C encodes protein C consisting of a C-terminal piece of the dystrophin sequence that is modified at its N-terminus by the intein C-terminal sequence (Int-C) and at its C-terminus by a tag sequence H. The tag sequences T, H, and S are a thioredoxin sequence, a poly-histidine sequence, and a S protein binding sequence, respectively, which are included for easier identification of the proteins.

The two-gene operon in each plasmid is behind an IPTG-inducible T7 promoter, which permits gene expression inside E. coli DE3 cells that harbor an IPTG-inducible T7 RNA polymerase gene. Upon induction by IPTG, each plasmid is expected to produce protein N and protein C. In addition, a spliced dystrophin protein (with the two dystrophin pieces fused together) would also be produced if protein trans-splicing occurs. All protein products can be identified easily by their distinct molecular masses determined by standard SDS-PAGE and by monitoring for the presence of the tag sequences (see FIG. 3). A spliced protein, if produced, is 69 kDa for all split gene constructs.

Figure 5:
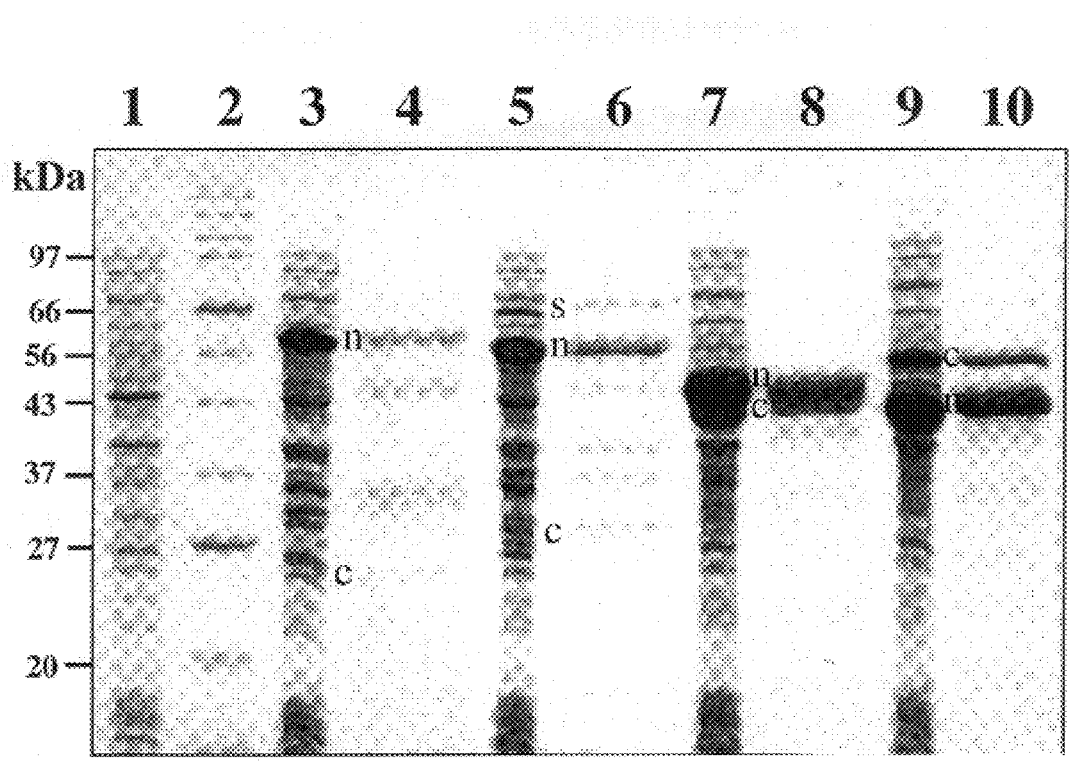
FIG. 5 shows a western blot showing trans-splicing of dystrophin in E. coli cells. Standard SDS-PAGE was used to analyze proteins from E. coli cells containing the split gene construct pDS1 (lanes 3 and 4), pDS2 (lanes 5 and 6), pDS3 (lanes 7 and 8), and pDS4 (lanes 9 and 10). Lanes 3, 5, 7 and 9 show total cellular proteins. Lanes 4, 6, 8 and 10 show purified proteins that all contain a poly-histidine tag. Protein N, protein C, and a spliced protein (if present) are marked by letters n, c and s, respectively. Lane 1 is total protein from control cells without protein production from the split genes. Lane 2 includes molecular weight markers whose sizes are shown on the left.

Among the above split gene constructs that were tested, only pDS2 produced a spliced dystrophin protein (FIG. 5). All plasmid constructs produced protein N and protein C, as expected. Protein N was produced more than protein C, because gene N is the first gene in the two-gene operon and is, therefore, more efficiently expressed. This is expected for this operon construct with incomplete translational coupling of the two genes. No spliced protein was observed in cells containing pDS1, pDS3, pDS4, and their variations, indicating that splitting the gene at S1, S3 and S4 locations did not support protein trans-splicing under the conditions tested. However, as demonstrated in Example 2, below, when the Ssp DnaB intein sequences of pDS4 are substituted with Ssp DnaE intein sequences, peptides expressed from this construct will trans-splice.

In cells containing pDS2, a spliced protein was detected, indicating that protein N and protein C underwent correct protein trans-splicing. Protein C was not completely incorporated into the spliced protein. The unspliced protein C, estimated to be about 50% of the total, may have been misfolded or trapped in inclusion bodies, which are known to occur when recombinant proteins are produced in bacterial cells in large quantities. Beside protein N, protein C, and the spliced protein, several other protein bands were also observed, which are most likely products of protein degradation that are also expected in bacterial cells. Modified versions of pDS2 and related constructs will be produced and tested for more efficient protein trans-splicing in E. coli cells and then in human cells.

The successful application of trans-splicing inteins to dystrophin makes it possible to transfer a functional dystrophin minigene in two pieces using an AAV vector, or in other vectors. The many unique advantages of AAV vector can now be exploited in a promising gene therapy for DMD and BMD. The size of each intein-modified dystrophin gene piece is reduced to within the maximum insert gene size of AAV vector, permitting the use of AAV vector in transferring the dystrophin minigene.

EXAMPLE 2

As shown above, in Example 1, the method of using an intein to splice together two dystrophin pieces was tested in E. coli cells using a 1.26 kbp gene fragment from the central rod domain of dystrophin (Becker form)(SEQ ID NO: 1). Out of the 4 plasmid-constructs (pDS1 through pDS4) that were tested, only pDS2 produced protein trans-splicing of the dystrophin pieces. In a subsequent experiment, an additional construct, pDS4E was prepared by splitting the same 1.26 kbp dystrophin gene fragment described in Example 1 at S4 and inserting the appropriate sequences of the Ssp DnaE intein. As with pDS2, the intein cassette included an IPTG- inducible T7 promoter, a ribosome-binding linker sequence and tag sequences. When expressed in E. coli , proteins N and C trans-spliced, to a similar degree as with pDS2. The complete sequence of the Ssp DnaE insert cassette in pDS4E is shown in FIG. 6 (SEQ ID NO: 6). The Ssp DnaE intein cassette present in pDS4E is a naturally occurring split intein consisting of an N-terminal piece and a C-terminal piece. The intein sequences a re shown in upper case letters in FIG. 6, the flanking dystrophin sequences and the spacer sequence between the intein pieces are shown in lower case letters in FIG. 6.

The above-described data demonstrates protein trans-splicing of intein-modified dystrophin pieces. A certain amount of protein misfolding may have occurred in the tests in E. coli cells, which explains why the protein splicing did not go to completion and some putative degradation products accumulated. Protein misfolding is known to be more pronounced in E. coli cells producing large amounts of recombinant proteins (over 20% of total protein in the cell), whereas it is less likely to be a problem in human muscle cells where a much smaller amount of dystrophin is needed (approximately 0.022% of total protein, according to one estimation).

It is also unlikely to be a problem if a small amount of unspliced dystrophin fragment accumulated in transduced muscle cells. The N-terminal piece of dystrophin is expected to be harmless in the presence of functional (spliced) dystrophin, because this is the case in muscle cells of unaffected heterozygote females, who produce a truncated N-terminal piece of dystrophin as well as a functional dystrophin. An unspliced C-terminal piece of dystrophin may or may not have undesirable effects. If it does, the gene promoters can be modified to produce an excess amount of the N-terminal piece that will drive the protein trans-splicing reaction to completely incorporate the C-terminal piece into spliced dystrophin.

Another potential concern is possible immune responses against the intein sequences that will be introduced as a foreign protein. However, this is not expected to be a major concern, because numerous in vivo gene transfer experiments using rAAV as the vectors have demonstrated an absence of host immune response to the foreign proteins, such as LacZ and GFP. To date there is no report of CTL reaction against transgene product triggered by rAAV-mediated gene delivery. In the unlikely event that a particular intein sequence may be unacceptably immunogenic, this problem may be avoided by changing to other available intein sequences.

EXAMPLE 3

Figure 7:
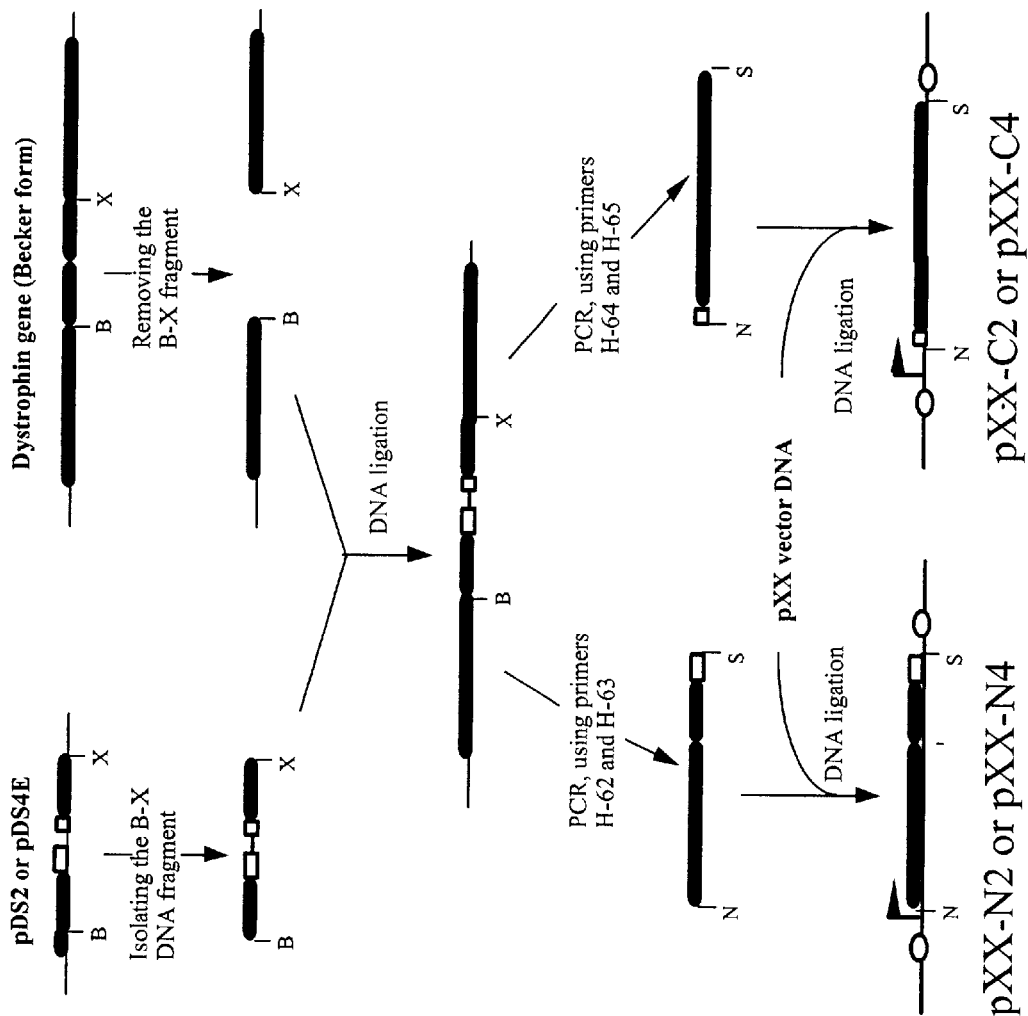
FIG. 7 is a schematic diagram showing the construction of plasmids pXX-N2, pXX-C2, pXX-N4 and pXX-C4.

A complete dystrophin-N gene and a complete dystrophin-C gene were synthesized and were placed in an AAV-based vector. The general scheme for the construction of these vectors is provided in FIG. 1. FIG. 7 shows, specifically, the procedure used to produce the complete dystrophin N- and C-genes and insertion of these genes into the AAV-based plasmid pXX-UF1, described herein and in Li et al. (1999).

In reference to FIG. 7, the sequences encoding the trans-splicing dystrophin pieces in pDS2 and pDS4E are used to produce pXX-N2, pXX-N4, pXX-C2 and pXX-C4 plasmids. The pXX-UF1 vector DNA is an AAV-based plasmid was cut with NotI and SalI restriction enzymes and the plasmid backbone, including functional AAV ITR sequences was purified. In FIG. 7, Dystrophin nucleotide sequences are indicated as black boxes, intein sequences are indicated as open boxes, B is the restriction enzyme BstXI, X is the restriction enzyme XhoI, N is the restriction enzyme NotI, and S is the restriction enzyme SalI. PCR primers used to amplify the intein modified C- and N-dystrophin gene portions are:

H-62 (5'-cgcgcagcggccgcacttttcaaaatgctttggtg-3', SEQ ID NO: 7),

H-63 (5'-gctcgcgtcgactacaattgtaaagaggagctttc-3', SEQ ID NO: 8),

H-64 (5'-gcgcagcggccgcttttcaaaatgcaattgtcaccagaaatag-3', SEQ ID NO: 9), and

H-65 (5'-cgcacgcgtcgactacattgtgtcctctctcattg-3', SEQ ID NO: 10).

The final constructs pXX-N2 and pXX-N4 produce protein N; pXX-C2 and pXX-C4 produce protein C, pXX-N2 complements pXX-C2 for trans-splicing, and pXX-N4 complements pXX-C4 for trans-splicing. In each of these constructs, expression of the intein- modified dystrophin portion is directed by a CMV promoter, as indicated by a flag in FIG. 7, and the AAV ITR sequences are indicated by the two flanking circles in FIG. 7.

As shown in FIG. 7, a 1.5-kbp BstXI-XhoI DNA fragment, which is a dystrophin sequence linked to intein sequences, was isolated from each of the pDS2 or pDS4E plasmid DNAs. A corresponding 1.0 kbp intein-free BstXI-XhoI fragment was removed from the plasmid encoding the unmodified dystrophin gene (Becker form). The 1.5 kbp pDS2 or pDS4E fragment was inserted into the BstXI-XhoI site of the plasmid encoding the unmodified dystrophin gene, producing a complete dystrophin gene linked to the intein sequences. The two resultant plasmids, containing the respective pDS2 and pDS4E intein-modified complete dystrophin genes were used as templates to produce the respective pDS2 and pDS4E protein N gene and the protein C gene by PCR. The N genes were amplified using the primer pairs H-62 and H-63. The C genes were amplified using the primer pairs H -64 and H-65. Since the primers included NotI and SalI restriction enzyme sites, the protein N and C genes were cut with those restriction enzymes and inserted into the NotI and SalI sites of pXX-UF1. The resulting plasmids, pXX-N2, pXX-N4, pXX-C2 and pXX-C4 contain the complete Becker form dystrophin N and C genes having the intein sequences and splice sites of the plasmids pDS2 and pDS4E under transcriptional control of the CMV promoter for expressing the N and C protein genes in eukaryotic cells. The constructs also contain plasmid sequences necessary for DNA propagation in *E. coli* cells, and AAV sequences (the ITRs) that are necessary for subsequent rAAV production and delivery into target cells.

The inserts of the plasmids, pXX-N2, pXX-N4, pXX-C2 and pXX-C4 were sequenced to verify the fidelity of the dystrophin and intein sequences thereof, the nucleotide sequences are as follows:

pXX-N2 (SEQ ID NOS: 11 and 12): The first 8 bases constitute the NotI cutting site, the last 6 bases constitute the SalI site. The triplet ATG (bases 19–21) is the start codon of protein N, the triplet TAG (bases 8–6 from the end) is the termination codon of protein N. Dystrophin sequences are in lower case letters, intein sequences are in upper case letters.
G c g g c c g c a c t t t t c a a a ATGctttg-
    gtgggaagaagtagaggactgttatgaaagagaa . . . (3180 bases) . .
                                    g a a a a c a g c c a a a a a a t c c t-
g a g a t c t c t a g a a g g c T G C A T C A G T G-
GAGATAGTTTGATCAG CTTGGCGAGCACAG-
GAAAAAGAGTTTCTATTAAAGATTTGTTAGATG
AAAAAGATTTTGARA TATGGGCAATTAATGAA-
C A G A C G A T G A A G C T A G A A T-
CAGCTAAAGTTAGTCGTGTATTTTGT ACTG-
GCAAAAAGCTAGTTTATATTCTAAAAACTCG
ACTAGGTAGAACTATCAAG
GCAACAGC AAATCATAGATTTTTAACTATTGATG-
G T T G G A A A A G A T T A G A T G A G C T A T C T T-
TAAAAGAGC ATATTGCTCTACCCCGTAAACTA-
GAAAGCTCCTCTTTACAATTGTAGtcgac pXX-C2 (SEQ ID NOS: 13 and 14): The first 8 bases constitute the NotI cutting site, the last 6 bases constitute the SalI site. The triplet ATG (bases 17–19) is the start codon of protein C, the triplet TAG (bases 8–6 from the end) is the termination codon of protein C. Dystrophin sequences are in lower case letters, intein sequences are in upper case letters.
G c g g c c g c t t t t c a a a ATGCAATTGT-
CACCAGAAATAGAAAAGTTGTCTCA-
GAGTGATATTT ACTGGGACTCCATCGTTTCTAT-
TACGGAGACTGGAGTCGAAGAGGTTTTTGAT
TTGACTGTG CCAGGACCACATAACTTTGTCGC-
CAATGACATCATTGTCCATAATtcggacgacgcagtact
gttacaaagacgtttggataacatgaacttcaagtggagtgaacttcggaaa . . .
(2670 bases) . . . gaggacacaatgtagtcgac pXX-N4 (SEQ ID NOS: 15 and 16): The first 8 bases constitute the NotI cutting site, the last 6 bases constitute the SalI site. The triplet ATG (bases 19–21) is the start codon of protein N, the triplet TAG (bases 8–6 from the end) is the termination codon of protein N. Dystrophin sequences are in lower case letters, intein sequences are in upper case letters.
G c g g c c g c a c t t t t c a a a ATGctttg-
    gtgggaagaagtagaggactgttatgaaagagaa . . . (2760 bases) . .
                              gtagatgtggcaaatgacttggccct-
g a a a c t t c t t c g c g a t t a t T G C C T C A G T T T T G G G A C
C G A A A T T T T A A C C G T T G A G T A C G G C-
C C A T T G C C C A T T G G C A A A A T T G T G A G T-
GAAGAAATTA ATTGTTCTGTGTACAGTGTTGATC-
CAGAAGGGAGAGTTTACACCCAGGCGATCG
CCCAATGG CATGACCGGGGAGAGCAGGAAG-
TATTGGAATATGAATTGGAAGATGGT-
TCAGTAATCCGAGC TACCTCTGACCACCGCTTTT-
TAACCACCGATTATCAACTGTTGGCGATCGAAGAA
ATTTTTG CTAGGCAACTGGACTTGTTGACTTTA-
G A A A A T A T T A A G C A A A C T G A A-
GAAGCTCTTGACAAC CATCGTCTTCCCTTTCCAT-
TACTTGACGCTGGAACAATTAAATAGtcgac pXX-C4 (SEQ ID NOS: 17 and 18): The first 8 bases constitute the NotI cutting site, the last 6 bases, constitute the SalI site. The triplet ATG (bases 17–19) is the start codon of protein C, the triplet TAG (bases 8–6 from the end) is the termination codon of protein C. Dystrophin sequences are in lower case letters, intein sequences are in upper case letters.

GcggccgcttttcaaaATGGTTAAAGT-
TATCGGTCGTCGTTCCCTCGGAGTGCAnAGAATAT
TTGATATTGGTCTTCCCCAAGACCAT-
AATTTTCTGCTAGCCAATGGGGC-
GATCGCCGCCAAT tccgcggatgataccagaaaagtcca-
catgataacagagaatatcaatgcctct . . . (3030 bases) . . .
atgagagaggacacaatgtagtcgac (SEQ ID No: 17 and 18)

In pXX-N2 (as in pDS2), the amino acid sequence at the dystrophin-intein junction is " . . . sqkilrslegCISGDSLISL . . . " (SEQ ID NO: 19), with dystrophin sequence in lower case letters and intein sequence in upper case letters.

In pXX-C2 (as in pDS2), the amino acid sequence at the dystrophin-intein junction is " . . . FVANDIIVHNsddavllqrr . . . " (SEQ ID NO: 20).

In pXX-N4 (as in pDS4E), which uses the Ssp DnaE mini-intein, the amino acid sequence at the dystrophin-intein junction is " . . . dlalkllrdyCLSFGTEILT . . . " (SEQ ID NO: 21).

In pXX-C4 (as in pDS4E), which uses the Ssp DnaE mini-intein, the amino acid sequence at the dystrophin-intein junction is " . . . LLANGAIAANsaddtrkvhm . . . " (SEQ ID NO: 22).

EXAMPLE 4

As described above, plasmids pXX-C2 and pXX-N2 were designed as a pair of C-half and N-half of the Becker-form dystrophin gene for trans-splicing. Similarly, plasmids pXX-C4 and pXX-N4 were designed as a different pair of C- half and N-half of the Becker-form dystrophin gene for trans-splicing.

Figure 8:
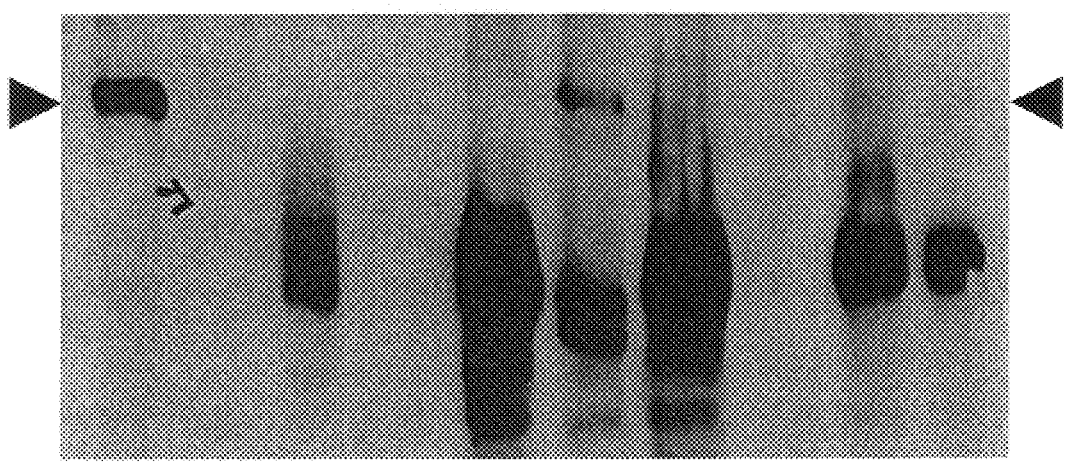
FIG. 8 shows a western blot showing trans-splicing of the complete dystrophin protein in transfected 293 cells according to Example 4.

To verify the trans-splicing activity shown in Examples 1 and 2 in *E. coli* cells, and to test if the C2/N2 and C4/N4 pairs can trans-splice in mammalian (human) cells, the plasmids containing the N and C genes were transfected into 293 cells. The plasmids were transfected into 293 cells as corresponding N and C gene pairs (i.e., pXX -C2 was co-transfected with pXX-N2), or individually as control experiments. If the gene products from the half-gene pairs successfully trans-spliced, the generation of the full-length Becker-form dystrophin protein should be detectable, which has approximately the combined molecular weight of the C-half and the N-half proteins. Transfection was performed by calcium phosphate precipitation according to standard methods. All transfections were performed on 10 cm plates of 293 cells at approximately 80% confluence. The intein sequences from the C-half and N-half of the respective dystrophin protein portions would be deleted during the process of trans-splicing. FIG. 8 shows the Western analysis of this experiment, using a monoclonal antibody against the C-half of the dystrophin protein, NCL-Dys2, commercially available from Novocastra Laboratories, Ltd. Of Burlingame, Calif. A secondary rabbit-anti-mouse antibody coupled with horseradish peroxidase (Sigma) was used to detect the prospective proteins with a chemiluminescent kit (NEN).

In reference to FIG. 8, lane 1 is the positive control which shows the full-length Becker dystrophin protein generated by transfection of 25 µg of the plasmid pCMV-Becker, containing the full-length Becker dystrophin gene. Lane 2 is the protein molecular weight marker, which cannot be detected by the antibody. Lane 3 is the transfection of 25 µg of pXX-C2, alone, and only the C-half dystrophin protein is detected. Lane 4 is the transfection of 25 µg of pXX-N2, alone, the N-half dystrophin being undetectable by the anti-C-terminus antibody. Lane 5 is the co-transfection of 12.5 µg of pXX-C2 and 12.5 µg of pXX-N2 in a 1:1 ratio. No obvious trans-spliced full-length Becker form dystrophin protein can be detected. However, in lane 6, when 4 µg of pXX-C2 and 21 µg of pXX-N2 were co-transfected in a 1:5 weight ratio (about a 1:5 molar ratio), a significant amount of full length trans-spliced Becker form dystrophin was detected as a 240 kD protein, as in the positive control in lane 1. It is believed that since the N-half protein is known to be very unstable, more N-protein must be produced in order to produce a substantial amount of trans-spliced protein.

In FIG. 8, lane 7 is a transfection of 25 µg of plasmid pXX-C4, alone, and a large amount of the C-half protein is dectectable. Lane 8 is a transfection of 25 µg of plasmid pXX-N4, alone, and the N-half dystrophin product cannot be detected by the anti-C-terminus antibody. Lane 9 is a co-transfection of 12.5 µg of plasmid pXX-C4 and 12.5 µg of plasmid pXX-N4. A small amount of full-length Becker form can be detected. Lane 10 is also a co-transfection of 4 µg of plasmid pXX-C4 and 21 µg of plasmid pXX-N4. However, no increase in trans-spliced Becker-form dystrophin is detectable. This suggests that C2 and N2 are more effective in trans-splicing than C4 and N4 when tested in mammalian cells.

EXAMPLE 5

Based on the positive results obtained by plasmid transfection of pXX-C2 and pXX-N2, rAAV viral vectors, in the form of viral particles separately carrying the C2 and N2 genes, could produce the full-length Becker form dystrophin protein after co-infection of the C2- and N2-carrying AAV viruses into 293 cell. AAV-C2 and AAV-N2 viral particles were produced by a three-plasmid co-transfection method in 293 cells as described before (Xiao et al. (1998)). Briefly, either plasmid pXX-C2 or plasmid pXX-N2 viral vector was co-transfected with packaging plasmid pXX2 and mini-adenovirus helper plasmid pXX6 into 293 cells. A total of 25 µg plasmid DNA (3 µg pXX2, 9 µg pC2 or pN2 and 13 µg pXX6) was dissolved in 1 ml of 0.25 M $CaCl_2$ and then quickly mixed with 1 ml of HBS buffer (50 mM HEPES, 280 mM NaCl and 1.5 mM $Na_2HPO_4$, pH 7.12) and added to the cells. Eight to 12 hours after transfection, the medium was replaced with fresh DMEM medium (Gibco) containing 10% FBS and antibiotics. The cells were harvested at 48 hours post-transfection unless specifically described. After low speed centrifugation on a table top centrifuge, the cell pellets were resuspended in 1 ml of 100 mM NaCl and 10 mM Tris-HCl (pH 8.5) and subjected to four cycles of freeze-thaw and removal of cell debris.

Large scale rAAV preparation and CsCl density gradient purification were carried out according to the previously published method (Snyder et al. (1996)). The DNA particle titers of AAV-C2 and AAV-N2 were determined by DNA dot blot method (Snyder et al. (1996)). The transducing unit (t.u.) titers were determined by immuno-fluorescent staining of 293 cells after infection with either AAV-C2 or AAV-N2 viruses. The monoclonal antibody against N-half dystrophin is NCL-Dys3 (Novocastra Laboratories Ltd.). The secondary antibody is a FITC-labeled (green fluorescent) rabbit-anti-mouse antibody (Novocastra Laboratories Ltd). After immunofluorescent staining, each green 293 cell is considered as being infected by one transducing unit (t.u.) of AAV-C2 or AAV-N2.

To detect the trans-spliced full-length Becker-form dystrophin protein after co-infection of AAV-C2 and AAV-N2 in human 293 cells, Western analyses were performed either using the anti-C-half antibody NCL-Dys2, or using the anti-N-half antibody NCL-Dys3. A secondary rabbit-antimouse antibody coupled with horseradish peroxidase (purchased from Sigma) was used to detect the prospective proteins with a chemiluminescent kit (NEN).

Figure 9A:
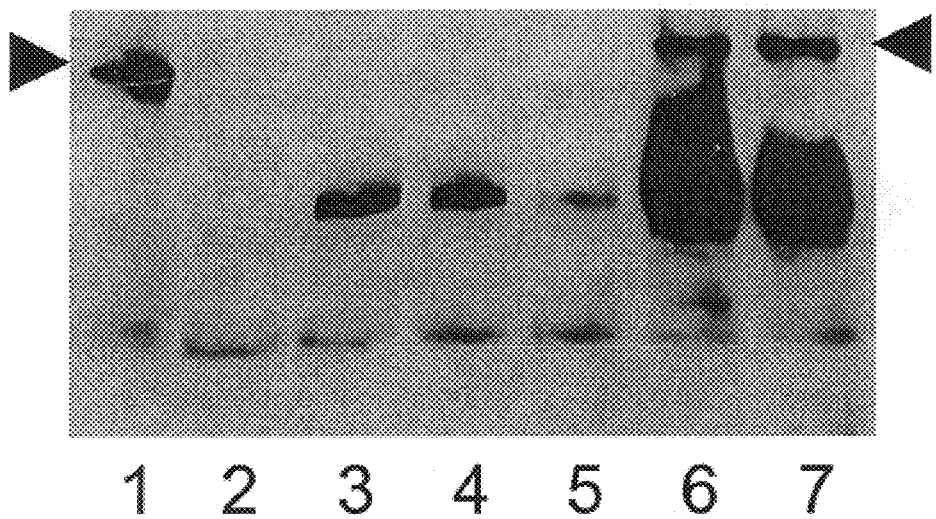
FIGS. 9A and 9B show western blots showing trans-splicing of the complete dystrophin protein in infected 293 cells according to Example 5. Anti-C-terminus antibody was used in the blot of FIG. 9A. Anti-N-terminus antibody was used in the blot of FIG. 9B.

FIG. 9 shows the Western analysis result using the anti-C-half antibody described above. Lane 1 is the full-length Becker dystrophin positive control obtained by transfecting 25 μg of the pCMV-Becker plasmid into the 293 cells. Lane 2 is 293 cells without any transfection or infection, as a negative control. Lane 3 is AAV-C2 virus infection alone at a multiplicity of infection (m.o.i.) of 10 transducing units (t.u.) per cell, and only the C-half dystrophin was detected. Lane 3 is the co-infection of AAV-C2 and AAV-N2 both at the m.o.i. of 10 t.u. per cell, and no Full-length Becker form dystrophin was detected. Lane 4 is the co-infection of AAV-C2 and AAV-N2 at the m.o.i. of 10 t.u. and 50 t.u. respectively, and no Full-length Becker form dystrophin was detected.

However, in lane 6, when the m.o.i. of AAV-C2 and AAV-N2 were increased to 250 t.u. per cell, significant amount of full-length Becker form dystrophin was generated as a result of trans-splicing. Similarly, in lane 7, when the m.o.i. of AAV-C2 was decreased to 50 t.u., while the m.o.i. of AAV-N2 was kept at 250 t.u, the same amount of full length Becker form dystropin was generated. These results demonstrated that full-length Becker form dystrophin protein can be generated through protein trans-splicing after co-infection of AAV vectors carrying the C and N halves of the dystrophin. In addition, our results showed that more N-half protein is needed for an efficient trans-splicing of Becker from dystrophin.

Figure 9B:
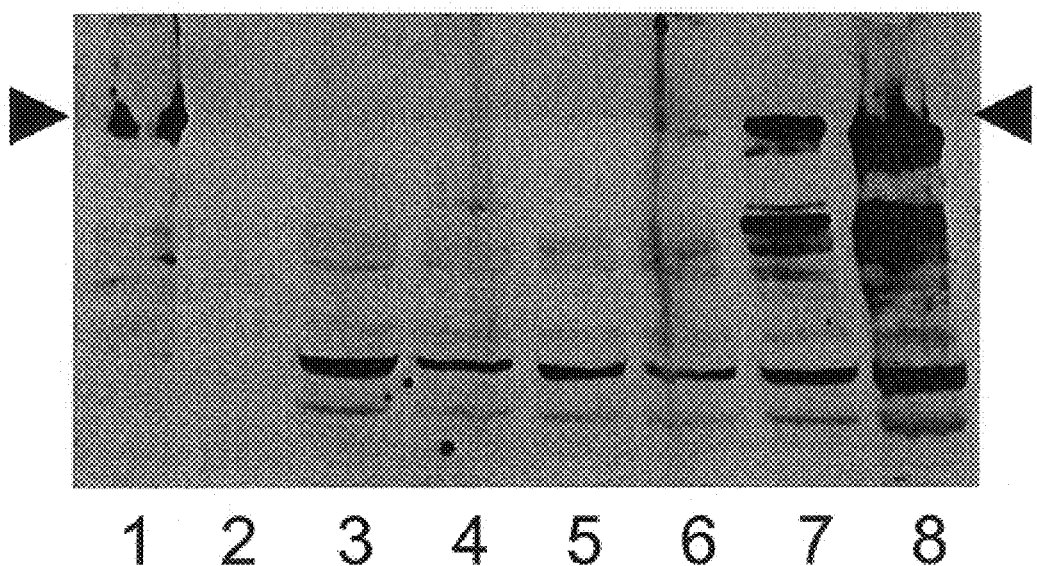

FIG. 9B shows the infection experiment using the anti-N-half antibody. Lane 1 is the full-length Becker dystrophin positive control obtained by transfecting the pCMV-Becker plasmid (25 μg) into the 293 cells. Lane 2 is the protein molecular weight marker, and no background staining can be seen. Lane 3 is 293 cells without any transfection or infection, as a negative control. Lane 4 is AAV-N2 virus infection alone at a multiplicity of infection (m.o.i.) of 10 transducing units (t.u.) per cell, and only the N-half dystrophin was detected. Lane 5 is the co-infection of AAV-C2 and AAV-N2 both at a m.o.i. of 10 t.u. per cell, and no Full-length Becker form dystrophin was detected. Lane 6 is the co-infection of AAV-C2 and AAV-N2 at the m.o.i. of 10 t.u. and 50 t.u. respectively, and small amount of Full-length Becker form dystrophin was detected. However, in lane 7, when the m.o.i. of AAV-C2 and AAV-N2 were increased to 250 t.u. per cell, significant amount of full-length Becker form dystrophin was generated as a result of trans-splicing. Similarly, in lane 8, when the m.o.i. of AAV-C2 was decreased to 50 t.u., while the m.o.i. of AAV-N2 was kept at 250 t.u, the same amount of full length Becker form dystropin was generated. It is notable that in lane 8 the protein is overloaded because the background staining was also higher. These results demonstrated that full-length Becker form dystrophin protein can be generated through protein trans-splicing after co-infection of AAV vectors carrying the C and N halves of the dystrophin. In addition, our results showed that more N-half protein is needed for an efficient trans-splicing of Becker from dystrophin.

EXAMPLE 6

AAV-C2 and AAV-N2 viral particles were co-injected into the muscle of mdx mice, a Duchenne muscular dystrophin animal model, to see if the half proteins generated from the AAV-C2 and AAV-N2 can join and form a Becker-form dystrophin, and correctly localize to the submembrane region of the muscle cells. Previous transgenic mouse studies showed that the Becker form dystrophin is fully functional in treating Duchenne muscular dystrophy in mdx mice (Phelps, S. F., M. A. Hauser, N. M. Cole, J. A. Rafael, R. T. Hinkle, J. A. Faulkner, and J. S. Chamberlain. 1995, Expression of full-length and truncated dystrophin mini-genes in transgenic mdx mice, Hum Mol Genet. 4:1251–8). Thus, if the Becker-form dystrophin is formed by trans-splicing, it should also be therapeutic. One of the methods to examine the presence of a functional dystrophin is immuno-fluorescent staining of the muscle samples with antibodies recognizing either the C or the N halves of the dystrophin protein. Both anti-C and anti-N antibodies should reveal the submembrane localization of the functional dystrophin protein, especially the N-half of the protein, which by itself can not localize to the submembrane region. In fact, numerous studies showed that mdx mouse has a nonsense (stop-codon) mutation in its dystrophin gene, which should produce an N-half dystrophin protein. However, this protein could not be detected due to its non-functional and unstable nature.

Figures 10A, 10B:
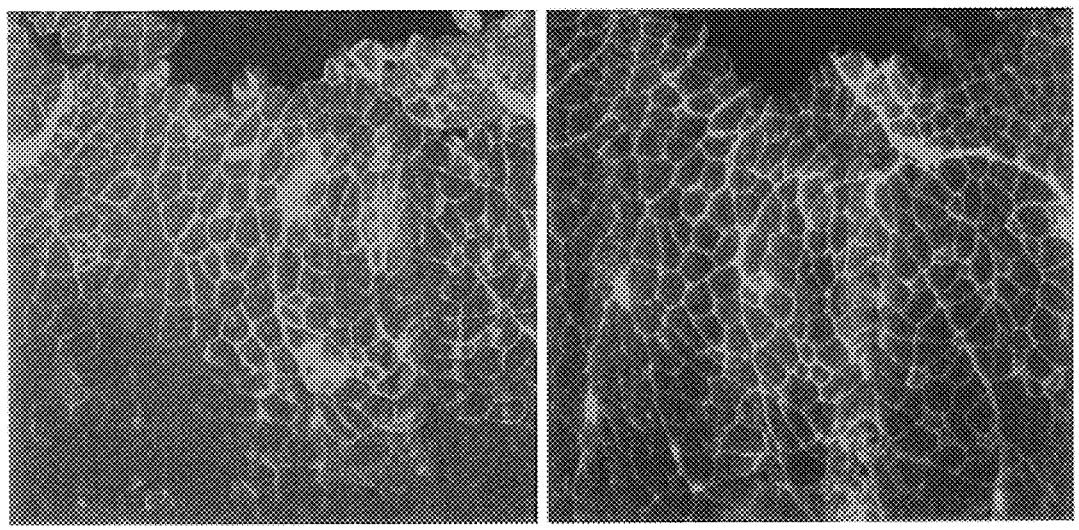
FIGS. 10A and 10B show immunofluorescent staining of infected muscle fibers of mdx mice according to Example 6.

Immunofluorescent staining of muscle samples from the mdx mice, which were co-injected with the AAV-C2 and AAV-N2 vectors, showed submembrane staining of dystrophin protein when either anti-C or anti-N antibodies were used. Briefly, muscle cryosections of 8 μm thickness were immunofluorescently stained with the Mouse-on-Mouse Kit from the Vector Laboratories (Burlingame, Calif.) according to the manufacturer's protocol, except that the cryosections were immediately treated with the blocking buffer without the fixation step (Li et al. (1998)). FIG. 10A shows the immunofluorescent staining using the anti-C-half antibody NCL-Dys2, which were then detected by a secondary rabbit-anti-mouse antibody labeled with red fluorescent dye Cy3 (Novocastra Laboratories Ltd, Burlingame, Calif.). FIG. 10B shows the immunofluorescent staining using the anti-N-half antibody NCL-Dys2, which was then detected by a secondary FITC-labeled rabbit-anti-mouse antibody labeled with green fluorescent dye (Novocastra Laboratories Ltd, Burlingame, Calif.). Both anti-C and anti-N antibodies revealed overlapping staining pattern in the muscle cross sections, suggesting that a large Becker-form dystrophin is generated by trans-splicing and correctly localized to the submembrane region of the muscle fibers. These results are consistent with the results shown in Example 5. The therapeutic effects on the mdx mouse muscle functions are currently under evaluation.

The method and viral particles described herein can be improved in several ways for more efficient protein trans-splicing and less side effects. Additional locations in the dystrophin central rod domain may be tested for better sites of gene splitting and intein fusion. Amino acids at or near the dystrophin-intein fusion points may be altered to attain better splicing while maintaining the dystrophin function. The intein sequence may be modified or substituted with other inteins to improve splicing efficiency. A humanized intein may be produced by modifying the HINT module of human hedgehog proteins. Further, more than one intein may be used to splice together more than two dystrophin pieces, so that a larger dystrophin with better function may be produced. The AAV construct may also be optimized for better gene transfer, expression and regulation. As discussed above, a number of AAV cloning vectors exist, including pSSV9, pTP-UF1, XX-UF1 and the "double D" vector of U.S. Pat. No. 5,869,305.

The efficiency of protein trans-splicing depends to a large degree on how strongly the two intein-containing half-proteins bind each other to allow the intein parts to reassemble. The efficiency can be increased by strengthening specific binding of the two intein-containing half-proteins. This can be achieved by adding to the intein sequences a pair of specially designed leucine zippers that are known to bring about specific and strong protein binding. Leucine zippers are used frequently in nature (including in mammalian cells) to achieve specific protein binding. For instance, a modified version of a pair of known leucine zippers that have been shown to bind each other specifically and strongly is being tested. Among the pair, one is an acidic coiled-coil and has an amino acid sequence AAQLEKELQALEKENAQLEWELQALEKELAQ (SEQ ID NO: 5), while the other is a basic coiled-coil and has a sequence AQLKKKLQALKKKNAQLKWKLQALKKKLAQG (SEQ ID NO: 6). The coding sequences for these leucine zippers can be readily synthesized by assembling oligonucleotides, and these coding sequences can easily be added to the intein-containing half-genes.

The leucine zippers can be linked directly to the intein sequences (rather than the dystrophin sequences), so that the mature (spliced) dystrophin will not have the leucine zippers. A short, flexible linker sequence will be placed between the leucine zipper and intein sequences, so that their structures do not interfere with each other. Specific and strong binding between the two leucine zippers will bring the two half-proteins together and maintain them together for a sufficient period of time to allow the two intein parts to assemble and carry out protein splicing. In doing so, the protein trans-splicing reaction is made more like a cis-splicing reaction that is intrinsically more efficient.

The above invention has been described with reference to the preferred embodiment. Obvious modifications and alterations will occur to others upon reading and understanding the preceding detailed description and the claims. It is intended that the invention be construed as including all such modifications and alterations.

We claim:

1. A method for preparing a trans-spliced peptide in vitro, comprising the steps of:
   a. providing (i) a first nucleic acid encoding and capable of expressing a first peptide in a suitable host cell, the first peptide having at its C-terminal end an N-terminal portion of a split intein and (ii) a second nucleic acid encoding and capable of expressing a second peptide in the host cell, the second peptide having at its N-terminal end a C-terminal portion of the same split intein, wherein the first and second nucleic acids are provided on the same or on different nucleic acid molecules; and
   b. producing the trans-spliced peptide by transferring the first nucleic acid and the second nucleic acid into the host cell, wherein at least one of the first nucleic acid and the second nucleic acid includes nucleotide sequences which allow for packaging of the nucleic acid into a recombinant Adeno-associated virus particle.

2. The method for preparing a trans-spliced peptide of claim 1, wherein the trans-spliced peptide is dystrophin, or a functional derivative thereof.

3. An isolated nucleic acid for use in preparing trans-spliced peptides, comprising a nucleotide sequence encoding a first peptide which is attached to suitable genetic regulatory elements for expression of the nucleotide sequence encoding the first peptide in a cell, the first peptide comprising:
   a. at its C-terminal end an N-terminal portion of a split intein which, when expressed in a suitable host cell in the presence of a second peptide having at its N-terminal end a C-terminal portion of the same split intein, will undergo trans-splicing with the second peptide to form a trans-spliced peptide; or
   b. at its N-terminal end a C-terminal portion of a split intein which, when expressed in a suitable host cell in the presence of a second peptide having at its C-terminal end an N-terminal portion of the same split intein, will undergo trans-splicing with the second peptide to form a trans-spliced peptide, wherein the nucleic acid further includes nucleotide sequences which allow for packaging of the nucleic acid into a recombinant Adeno-associated virus particle such that said nucleic acid can be transferred into a host cell by an Adeno-associated virus particle.

4. The nucleic acid of claim 3, wherein the trans-spliced peptide is dystrophin, or a functional derivative thereof.

5. A composition comprising the nucleic acid of claim 3, and a pharmaceutically acceptable excipient.

6. The composition of claim 5, wherein the nucleic acid is packaged in an Adeno-Associated Virus particle and the trans-spliced peptide is dystrophin or a functional derivative thereof.

7. A kit, comprising: a sealed vessel and the nucleic acid of claim 3 within the sealed vessel.

8. The method of claim 1, wherein the nucleic acid is transferred to the host cell by an Adeno-associated virus particle.

9. A modified cell containing a nucleic acid as claimed in claim 3.

* * * * *